US006156725A

United States Patent [19]
Mukherjee et al.

[11] Patent Number: 6,156,725
[45] Date of Patent: Dec. 5, 2000

[54] DRUG FOR THE TREATMENT OF CANCER

[75] Inventors: Rama Mukherjee; Manu Jaggi, both of New Delhi, India

[73] Assignee: National Institute of Immunology, New Delhi, India

[21] Appl. No.: 08/727,679

[22] Filed: Oct. 8, 1996

[30] Foreign Application Priority Data

Aug. 16, 1996 [IN] India ........................................ 1822/96

[51] Int. Cl.$^7$ .................................................. A61K 38/00
[52] U.S. Cl. .................................. 514/12; 514/13; 514/14; 514/908; 530/309; 530/311; 530/324; 530/327; 530/328
[58] Field of Search .............................. 514/12–14, 908; 530/309, 311, 324, 327, 328

[56] References Cited

U.S. PATENT DOCUMENTS

| | | | |
|---|---|---|---|
| 5,273,963 | 12/1993 | Moody | 514/12 |
| 5,434,132 | 7/1995 | Rozengurt | 514/2 |

FOREIGN PATENT DOCUMENTS

| | | |
|---|---|---|
| 0309297 | 3/1989 | European Pat. Off. . |
| 9003980 | 4/1990 | WIPO . |
| 9102745 | 3/1991 | WIPO . |
| 9521194 | 8/1995 | WIPO . |

OTHER PUBLICATIONS

Liebow, C., et al. "Somatostatin analogues inhibit growth of pancreatic cancer by stimulating tyrosine phosphatase." Proc. of the Nat. Acad. of Sciences of the USA, vol. 86, No. 6 (1989)pp. 2003–2007.

Pinski, J., et al. "Inhibition of Growth of MKN45 Human Gastric–Carcinoma Xenografts in Nude Mice by Treatment with Bombesin/Gastrin–Releasing–Peptide Antagonist (RC–3095) and Somatostatin Analogue RC–160." International Journal of Cancer, vol. 57, No. 4 (1994) pp. 574–580.

E. Bombardieri, et al., "Somatostatin Receptor Imaging of Small Cell Lung Cancer . . . Scintigraphy," European Journal of Cancer, vol. 31A, No. 2, pp.184–188, 1995.

J. Pinski, et al., "Somatostatin Analogues And Bombesin/Gastrin . . . In Vitro And In Vivo," Peptide Analogues In Glioblastomas, vol. , pp.5895–5901, (1994).

P.A. Bunn, Jr., et al., "Effects of Neuropeptide Analogues on . . . Cancer Cell Lines," Cancer Research 54, pp. 3602–3610, Jul. 1, 1994.

G. Lilling, et al., "Inhibition of Human Neuroblastoma . . . VIP Antagonist," Journal of Molecular Neuroscience, vol. 5, 1994/1995, pp. 231–239.

H. Reile, et al., "Characterization of High–Affinity Receptors for Bombesin/Gastrin Releasing . . . By Tumor Cells," The Prostate 25:29–38, (1994).

I. Virgolini, M.D., et al., "Vasoactive Intestinal Peptide–Receptor . . . Endocrine Tumors," The New England Journal of Medicine, vol. 331, No. 17, pp. 1116–1121, Oct. 27, 1994.

K. Frank–Raue, et al., "Somatostatin Receptor Imaging in Persistent Medullary Thyroid Carcinoma," Clinical Endocrinology (1995) 42, pp. 31–37.

Gabor Halmos, et al., "Characterization of Bombesin/Gastrin–Releasing Peptide . . . Gastric Cancer," Cancer Letters 85 (1994), pp. 111–118.

Antal Orosz, et al., "New Short–Chain Analogs of Substance–P . . . Cells In Vitro and In Vivo," Int. J. Cancer, 60, pp. 82–87, (1995).

Karoly Szepeshazi, et al., "Combination of Nitrosamine–Induced . . . Bombesin/GRP Antagonist," Int'l. Journal of Pancreatology, vol. 16, Nos. 2–3, pp. 141–149, Oct.–Dec. 1994.

P. Heinz–Erian, et al., "Characterization of a New Group of Substituted Substance P . . . Antagonists," Abstracts of Papers, pp. 1455, May 1986.

Tim Mosmann, "Rapid Colorimetric Assay for Cellular Growth and . . . Cytotoxicity Assays," Journal of Immunological Methods, 65, (1983), pp. 55–63.

I. Zachary, et al., "Bombesin, Vasopressin, and Endothelin Rapidly Stimulate . . . 3T3 Cells," Proc. Natl. Acad. Sci. USA, vol. 88, pp. 4577–4581, Jun. 1991.

I. Gozes, et al., "Vasoactive Intestinal Peptide Potentiates Sexual Behavior . . . . Antagonist," Endocrinology, vol. 125, No. 6, pp. 2945–2949, 1989.

P. Woll, et al., "[D–ARG$^1$,D–PHE$^5$,D–TRP$^{7,9}$, LEU$^{11}$] Substance P, A Potent Bombesin . . . In Vitro," Proc. Natl. Acad. Sci. USA, vol. 85, pp. 1859–1863, Mar. 1988.

M. Jaggi, et al., "New, Sensitive and Specific Elisa for Detection . . . Supernatants," Journal of Immunoassay, 15(2), pp. 129–146 (1994).

K. Gulya, et al., "Cyclic Somatostatin Octapeptide Analogues With High . . . Opioid Receptors," Life Sciences, vol. 38, No. 24, pp.2221–2229, 1986.

M. Brown, et al., "Somatostatin: Analogs With Selected Biological Activities," Science, vol. 196, pp.1467–1469, (1977).

(List continued on next page.)

Primary Examiner—Cecilia J. Tsang
Assistant Examiner—C. Delacroix-Muirheid
Attorney, Agent, or Firm—Ladas & Parry

[57] ABSTRACT

A pharmaceutical composition useful for killing or inhibiting multiplication of cancer cells. It is expected that the pharmaceutical composition will be useful in preventing, inhibiting, or modulating the hypersecretion of VIP, somatostatin, bombesin, Substance P, or a combination of VIP, somatostatin, bombesin, or Substance P. The composition may suitably comprise, consist of, or consist essentially of a therapeutically effective combination of peptide analogs of somatostatin, VIP, bombesin, and Substance P. Also provided is a method of treatment for humans or other animals suffering from cancer, the method comprising administering a therapeutically effective dose of the pharmaceutical composition so as to kill or inhibit the multiplication of cancer cells. The method of treatment may be particularly useful in the treatment of cancers of the colon and rectum. Also provided is a method of treatment for humans or animals having hypersecretion or modulation of VIP, somatostatin, bombesin, Substance P, or a combination of VIP, somatostatin, bombesin, or Substance P.

20 Claims, 9 Drawing Sheets

OTHER PUBLICATIONS

J. T. Pelton, et al., "Design and Synthesis of Conformationally Constrained Somatostatin . . . Receptors," J. Med. Chem. 1986, 29, pp. 2370–2375.

M. Jaggi, et al., "Establishment of Tumorigenic Cell Lines From Biopsies . . . Adenocarcinomas," Journal of Basic & Applied Biomedicine (1995) 3 (4), pp. 27–35.

Frucht et al., *Cancer Res.*, 52(5), 1114–22, 1992.

SEQUENCE LISTING

<160> NUMBER OF SEQ ID NOS: 46

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence: This
      peptide was synthetically generated.

<400> SEQUENCE: 1

Lys Pro Arg Arg Pro Tyr Thr Asp Asn Tyr Thr Arg Leu Arg Lys Gln
 1               5                  10                  15
Met Ala Val Lys Lys Tyr Leu Asn Ser Ile Leu Asn
             20                  25

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.

<400> SEQUENCE: 2

Leu Met Tyr Pro Thr Tyr Leu Lys
 1               5

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: This
      peptide was synthetically generated.

<400> SEQUENCE: 3

Tyr Thr Arg Leu Arg Lys Gln Met Ala Val Lys Lys Tyr Leu Asn Ser
 1               5                  10                  15
Ile Leu Asn

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: This
      peptide was synthetically generated.

<400> SEQUENCE: 4

Phe Thr Asp Asn Tyr Thr Arg Leu Arg Lys Gln Met Ala Val Lys Lys
 1               5                  10                  15
Tyr Leu Asn Ser Ile Leu Asn
             20

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: This
      peptide was synthetically generated.

<400> SEQUENCE: 5

Tyr Gly Cys Lys Asn Phe Phe Trp Lys Thr Phe Thr Ser Cys
 1               5                  10

```
<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence:  This
      peptide was synthetically generated.

<400> SEQUENCE: 6

Ala Gly Cys Lys Asn Phe Phe Trp Lys Thr Tyr Thr Ser Cys
 1               5                  10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /products = "L-pyroglutamic acid"/label = pGlu
<220> FEATURE:
<221> NAME/KEY: SITE
<222> LOCATION: (13)..(14)
<223> OTHER INFORMATION: /products = "OTHER"/note = "surrogate bond
      followed by (CH2NH)"

<400> SEQUENCE: 7

Lys Gln Arg Leu Gly Asn Gln Trp Ala Val Gly His Leu Leu
 1               5                  10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product = "pyroglutamic acid" /label = Pyr
<220> FEATURE:
<221> NAME/KEY: SITE
<222> LOCATION: (13)..(14)
<223> OTHER INFORMATION: /products = "OTHER" / note = "reduced bond"

<400> SEQUENCE: 8

Xaa Gln Arg Leu Gly Asn Gln Trp Ala Val Gly His Leu Leu
 1               5                  10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence:  This
      peptide was synthetically generated.

<400> SEQUENCE: 9

Trp Ala Val Gly His Leu Met
 1               5

<210> SEQ ID NO 10
<211> LENGTH: 14
<212> TYPE: PRT
<213> ORGANISM: Artificial Sequence
<220> FEATURE:
```

```
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product = "L-pyroglutamic acid" /label = pGlu

<400> SEQUENCE: 10

Xaa Gln Arg Tyr Gly Asn Gln Trp Ala Val Gly His Leu Met
 1               5                  10

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (6)
<223> OTHER INFORMATION: /product = "4-Chloro-D-phenyalanine" /label =
      "4-Cl-D-Phe"

<400> SEQUENCE: 11

His Ser Asp Ala Val Xaa Thr Asp Asn Tyr Thr Arg Leu Arg Lys Gln
 1               5                  10                  15
Leu Ala Val Lys Lys Tyr Leu Asn Ser Ile Leu Asn
            20                  25

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (1)
<223> OTHER INFORMATION: /product = "D-phenylalanine / label = "D-Phe"
<220> FEATURE:
<221> NAME/KEY: MOD_RES
<222> LOCATION: (4)
<223> OTHER INFORMATION: /product = "D-Trytophan" /label = "D-Trp"
<220> FEATURE:
<221> NAME/KEY: MOD_RES
<222> LOCATION: (5)
<223> OTHER INFORMATION: /product = "Ornithine" /label = "Orn"
<220> FEATURE:
<221> NAME/KEY: MOD_RES
<222> LOCATION: (7)
<223> OTHER INFORMATION: /product = "Penicillamine" /label = "Pen"

<400> SEQUENCE: 12

Xaa Cys Tyr Xaa Xaa Thr Xaa Thr
 1               5

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (8)
<223> OTHER INFORMATION: /product = "D-Tryptophan" /label = "D-Trp"
<220> FEATURE:
<221> NAME/KEY: MOD_RES
<222> LOCATION: (13)..(14)
<223> OTHER INFORMATION: /product = Note: disulfide bridges: 3-14
```

```
<220> FEATURE:
<221> NAME/KEY: MOD_RES
<222> LOCATION: ()..)
<223> OTHER INFORMATION: /product = "D-Cysteine" /label = "D-Cys"

<400> SEQUENCE: 13

Ala Gly Cys Lys Asn Phe Phe Xaa Lys Thr Phe Thr Ser Xaa
 1               5                  10

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product = "D-phenylalanine" /label = "D-Phe"
<220> FEATURE:
<221> NAME/KEY: MOD_RES
<222> LOCATION: (8)
<223> OTHER INFORMATION: /product = "Leucine N-ethylamide" /label =
      "Leu-NHet"

<400> SEQUENCE: 14

Xaa Gln Trp Ala Val Gly His Xaa
 1               5

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product = "D-Arginine" /label = "D-Arg"
<220> FEATURE:
<221> NAME/KEY: MOD_RES
<222> LOCATION: (5)
<223> OTHER INFORMATION: /product = "D-Phenylalanine" /label = "D-Phe"
<220> FEATURE:
<221> NAME/KEY: MOD_RES
<222> LOCATION: (9)
<223> OTHER INFORMATION: /product = "D-Tryptophan" /label = "D-Trp"
<220> FEATURE:
<221> NAME/KEY: MOD_RES
<222> LOCATION: (9)
<223> OTHER INFORMATION: /product = "D-Tryptophan" /label = "D-Trp"

<400> SEQUENCE: 15

Xaa Pro Lys Pro Xaa Gln Xaa Phe Xaa Leu Leu
 1               5                  10

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product = "N-Acetylated Tyrosine" /label =
      "Ac-Tyr"
<220> FEATURE:
<221> NAME/KEY: MOD_RES
<222> LOCATION: (2)
```

```
<223> OTHER INFORMATION: /product = "D-Phenylalanine" /label = "D-Phe"

<400> SEQUENCE: 16

Xaa Xaa Asp Ala Ile Phe Thr Asn Ser Tyr Arg Lys Val Leu Gly Gln
  1               5                  10                  15
Leu Ser Ala Arg Lys Leu Leu Gln Asp Ile Met Ser Arg
                 20                  25

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (8)
<223> OTHER INFORMATION: /product = "D-Tryptophan" /label = "D-Trp"

<400> SEQUENCE: 17

Ala Gly Cys Lys Asn Phe Phe Xaa Lys Thr Phe Thr Ser Cys
  1               5                  10

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (1)
<223> OTHER INFORMATION: /product = "D-phenylalanine" /label = "D-Phe"
<220> FEATURE:
<221> NAME/KEY: MOD_RES
<222> LOCATION: (4)
<223> OTHER INFORMATION: /product = "D-Tryptophan" /label = "D-Trp"
<220> FEATURE:
<221> NAME/KEY: MOD_RES
<222> LOCATION: (7)
<223> OTHER INFORMATION: /product = "Penicillamine" /label = "Pen"

<400> SEQUENCE: 18

Xaa Cys Tyr Xaa Arg Thr Xaa Thr
  1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (1)
<223> OTHER INFORMATION: /product = "-(2-Naphthyl)-D-Alanine" /label =
      "-(2-Naphthyl)-D-Ala"
<220> FEATURE:
<221> NAME/KEY: MOD_RES
<222> LOCATION: (4)
<223> OTHER INFORMATION: /product = "D-Tryptophan" /label = "D-Trp"

<400> SEQUENCE: 19

Xaa Cys Tyr Xaa Lys Val Cys Thr
  1               5

<210> SEQ ID NO 20
<211> LENGTH: 7
```

```
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product = "D-phenylalanine" /label = "D-Phe"
<220> FEATURE:
<221> NAME/KEY: MOD_RES
<222> LOCATION: (4)
<223> OTHER INFORMATION: /product = "D-Tryptophan" /label = "D-Trp"

<400> SEQUENCE: 20

Xaa Cys Tyr Xaa Lys Cys Thr
 1               5

<210> SEQ ID NO 21
<211> LENGTH: 28
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (22)
<223> OTHER INFORMATION: /product = "D-Tryptophan" /label = "D-Trp"

<400> SEQUENCE: 21

Ser Ala Asn Ser Asn Pro Ala Leu Ala Pro Arg Glu Arg Lys Ala Gly
 1               5                  10                  15
Cys Lys Asn Phe Phe Xaa Lys Thr Tyr Thr Ser Cys
                20                  25

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (8)
<223> OTHER INFORMATION: /product = "D-Tryptophan" /label  "D-Trp"

<400> SEQUENCE: 22

Ala Gly Cys Lys Asn Phe Phe Xaa Lys Thr Tyr Thr Ser Cys
 1               5                  10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (11)
<223> OTHER INFORMATION: /product = "D-Tryptophan" /label = "D-Trp"

<400> SEQUENCE: 23

Ala Gly Cys Lys Asn Phe Phe Trp Leu Thr Xaa Thr Ser Cys
 1               5                  10

<210> SEQ ID NO 24
<211> LENGTH: 8
<212> TYPE: PRT
```

```
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (1)
<223> OTHER INFORMATION: /product = "-(2-Naphthyl)-D-Alanine" /label =
      "-(2-Naphthyl)-D-Ala"
<220> FEATURE:
<221> NAME/KEY: MOD_RES
<222> LOCATION: (4)
<223> OTHER INFORMATION: /product = "D-Tryptophan" /label = "D-Trp"

<400> SEQUENCE: 24

Xaa Cys Tyr Xaa Lys Val Cys Thr
 1               5

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (6)
<223> OTHER INFORMATION: /product = "D-Tryptophan" /label = "D-Trp"

<400> SEQUENCE: 25

Cys His His Phe Phe Xaa Lys Thr Phe Thr Ser Cys
 1               5                  10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (1)
<223> OTHER INFORMATION: /product = "D-Arginine" /label = "D-Arg"
<220> FEATURE:
<221> NAME/KEY: MOD_RES
<222> LOCATION: (2)
<223> OTHER INFORMATION: /product = "D-Proline" /label = "D-Pro"
<220> FEATURE:
<221> NAME/KEY: MOD_RES
<222> LOCATION: (7)
<223> OTHER INFORMATION: /product = "D-Tryptophan" /label = "D-Trp"
<220> FEATURE:
<221> NAME/KEY: MOD_RES
<222> LOCATION: (9)
<223> OTHER INFORMATION: /product = "D-Tryptophan" /label = "D-Trp"

<400> SEQUENCE: 26

Xaa Xaa Lys Pro Gln Gln Xaa Phe Xaa Leu Leu
 1               5                  10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (1)
<223> OTHER INFORMATION: /product = "D-Pyroglutamic Acid" /label =
```

"D-Pyr"
<220> FEATURE:
<221> NAME/KEY: MOD_RES
<222> LOCATION: (12)
<223> OTHER INFORMATION: /product = "D-Phenylalanine" /label = "D-Phe"

<400> SEQUENCE: 27

Xaa Gln Arg Leu Gly Asn Gln Trp Ala Val Gly Xaa Leu Leu
 1               5                  10

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (1)
<223> OTHER INFORMATION: /product = "Pyroglutamic Acid" /label = "pGlu"
<220> FEATURE:
<221> NAME/KEY: MOD_RES
<222> LOCATION: (12)
<223> OTHER INFORMATION: /product = "D-Phenylalanine" /label = "D-Phe"

<400> SEQUENCE: 28

Xaa Gln Arg Tyr Gly Asn Gln Trp Ala Val Gly Xaa Leu Met
 1               5                  10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (1)
<223> OTHER INFORMATION: /product = "Pyroglutamic Acid" /label = "pGlu"
<220> FEATURE:
<221> NAME/KEY: MOD_RES
<222> LOCATION: (12)
<223> OTHER INFORMATION: /product = "D-Phenylalanine" /label = "D-Phe"

<400> SEQUENCE: 29

Xaa Gln Arg Leu Gly Asn Gln Trp Ala Val Gly Xaa Leu Met
 1               5                  10

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (1)
<223> OTHER INFORMATION: /product = "3-Phenylpropionyl" /label =
      "Deamino-Phe"
<220> FEATURE:
<221> NAME/KEY: MOD_RES
<222> LOCATION: (6)
<223> OTHER INFORMATION: /product = "D-Alanine" /label = "D-Ala
<220> FEATURE:
<221> NAME/KEY: MOD_RES
<222> LOCATION: (8)
<223> OTHER INFORMATION: /products = "D-Proline-(CH2NH)-Phe-NH2" Note:
      "peptide bond between D-Pro and Phe is replaced by
      CH2NH" /label = "D-Pro-[CH2NH]-Phe-NH2"

-continued

<400> SEQUENCE: 30

Xaa His Trp Ala Val Xaa His Xaa
 1               5

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product = "D-Arginine" /label = "D-Arg"
<220> FEATURE:
<221> NAME/KEY: MOD_RES
<222> LOCATION: (7)
<223> OTHER INFORMATION: /product = "D-Tryptophan" /label = "D-Trp"
<220> FEATURE:
<221> NAME/KEY: MOD_RES
<222> LOCATION: (9)
<223> OTHER INFORMATION: /product = "D-Tryptophan" /label = "D-Trp"

<400> SEQUENCE: 31

Xaa Pro Lys Pro Gln Gln Xaa Phe Xaa Leu Leu
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product = "H-D-Lysine (Nicotinoyl)" /label =
      "D-NicLys"
<220> FEATURE:
<221> NAME/KEY: MOD_RES
<222> LOCATION: (4)
<223> OTHER INFORMATION: /product = "-(3-Pyridyl)-Alanine" /label =
      "Pal"
<220> FEATURE:
<221> NAME/KEY: MOD_RES
<222> LOCATION: (6)
<223> OTHER INFORMATION: /product = "-3,4-Dichloro-d-Phenylalanine"
      /label
      = "D-Cl2Phe"
<220> FEATURE:
<221> NAME/KEY: MOD_RES
<222> LOCATION: (8)
<223> OTHER INFORMATION: /product = "D-Tryptophan" /label = "D-Trp
<220> FEATURE:
<221> NAME/KEY: MOD_RES
<222> LOCATION: (10)
<223> OTHER INFORMATION: /product = "D-Tryptophan" /label = "D-Trp
<220> FEATURE:
<221> NAME/KEY: MOD_RES
<222> LOCATION: (12)
<223> OTHER INFORMATION: /product = "Norleucine" /label = "Nle"

<400> SEQUENCE: 32

Xaa Pro Thr Xaa Pro Xaa Asn Xaa Phe Xaa Leu Xaa
 1               5                  10

<210> SEQ ID NO 33
<211> LENGTH: 11
<212> TYPE: PRT
<213> ORGANISM: Artificial Sequence
<220> FEATURE:

```
<223> OTHER INFORMATION: Description of Artificial Sequence:  This
      peptide was synthetically generated.
<220> FEATURE:
<221> NAME/KEY: MOD_RES
<222> LOCATION: (2)
<223> OTHER INFORMATION: /product = "D-Proline" /label = "D-Pro"
<220> FEATURE:
<221> NAME/KEY: MOD_RES
<222> LOCATION: (7)
<223> OTHER INFORMATION: /product = "D-Phenylalanine" /label = "D-Phe"
<220> FEATURE:
<221> NAME/KEY: MOD_RES
<222> LOCATION: (9)
<223> OTHER INFORMATION: /product = "D-Tryptophan" /label = "D-Trp"

<400> SEQUENCE: 33

Arg Xaa Lys Pro Gln Gln Xaa Phe Xaa Leu Met
 1               5                  10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (2)
<223> OTHER INFORMATION: /product = "D-Proline" /label = "D-Pro"
<220> FEATURE:
<221> NAME/KEY: MOD_RES
<222> LOCATION: (7)
<223> OTHER INFORMATION: /product = "D-Tryptophan" /label = "D-Trp"
<220> FEATURE:
<221> NAME/KEY: MOD_RES
<222> LOCATION: (9)
<223> OTHER INFORMATION: /product = "D-Tryptophan" /label = "D-Trp"

<400> SEQUENCE: 34

Arg Xaa Xaa Pro Gln Gln Xaa Phe Xaa Leu Met
 1               5                  10

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (1)
<223> OTHER INFORMATION: /product = "D-Proline" /label = "D-Pro"
<220> FEATURE:
<221> NAME/KEY: MOD_RES
<222> LOCATION: (4)
<223> OTHER INFORMATION: /product = "D-Tryptophan" /label = "D-Trp"
<220> FEATURE:
<221> NAME/KEY: MOD_RES
<222> LOCATION: (6)
<223> OTHER INFORMATION: /product = "D-Tryptophan" /label = "D-Trp

<400> SEQUENCE: 35

Xaa Gln Gln Xaa Phe Xaa Leu Met
 1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence:  This
```

```
         peptide was synthetically generated.
<220> FEATURE:
<221> NAME/KEY: MOD_RES
<222> LOCATION: (2)
<223> OTHER INFORMATION: /product = "D-Tryptophan" /label = "D-Trp"
<220> FEATURE:
<221> NAME/KEY: MOD_RES
<222> LOCATION: (3)
<223> OTHER INFORMATION: /product = "N-methyl Phenylalanine" /label =
      "Me-Phe"
<220> FEATURE:
<221> NAME/KEY: MOD_RES
<222> LOCATION: (4)
<223> OTHER INFORMATION: /product = "D-Tryptophan" /label = "D-Trp"

<400> SEQUENCE: 36

Arg Xaa Xaa Xaa Leu Met
 1               5

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (1)
<223> OTHER INFORMATION: /product = "D-arginine" /label = "D-Arg"
<220> FEATURE:
<221> NAME/KEY: MOD_RES
<222> LOCATION: (5)
<223> OTHER INFORMATION: /product = "D-Phenylalanine" /label = "D-Phe"
<220> FEATURE:
<221> NAME/KEY: MOD_RES
<222> LOCATION: (7)
<223> OTHER INFORMATION: /product = "D-Tryptophan" /label = "D-Trp"
<220> FEATURE:
<221> NAME/KEY: MOD_RES
<222> LOCATION: (9)
<223> OTHER INFORMATION: /product = "D-Tryptophan" /label = "D-Trp"

<400> SEQUENCE: 37

Xaa Pro Lys Pro Xaa Gln Xaa Phe Xaa Leu Leu
 1               5                  10

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (1)
<223> OTHER INFORMATION: /product = "D-Proline" /label = "D-Pro"
<220> FEATURE:
<221> NAME/KEY: MOD_RES
<222> LOCATION: (4)
<223> OTHER INFORMATION: /product = "D-Tryptophan" /label = "D-Trp"
<220> FEATURE:
<221> NAME/KEY: MOD_RES
<222> LOCATION: (6)
<223> OTHER INFORMATION: /product = "D-Tryptophan" /label = "D-Trp"
<220> FEATURE:
<221> NAME/KEY: MOD_RES
<222> LOCATION: (7)
<223> OTHER INFORMATION: /product = "D-Tryptophan" /label = "D-Trp"

<400> SEQUENCE: 38

Xaa Gln Gln Xaa Phe Xaa Xaa Phe
 1               5
```

```
<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product = "D-Proline" /label = "D-Pro"
<220> FEATURE:
<221> NAME/KEY: MOD_RES
<222> LOCATION: (4)
<223> OTHER INFORMATION: /product = "D-Tryptophan" /label = "D-Trp"
<220> FEATURE:
<221> NAME/KEY: MOD_RES
<222> LOCATION: (6)
<223> OTHER INFORMATION: /product = "D-Tryptophan" /label = "D-Trp"
<220> FEATURE:
<221> NAME/KEY: MOD_RES
<222> LOCATION: (7)
<223> OTHER INFORMATION: /product = "D-Tryptophan" /label = "D-Trp"

<400> SEQUENCE: 39

Xaa Gln Gln Xaa Phe Xaa Xaa Met
 1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product = "D-Proline" /label = "D-Pro"
<220> FEATURE:
<221> NAME/KEY: MOD_RES
<222> LOCATION: (4)
<223> OTHER INFORMATION: /product "D-Tryptophan" /label = "D-Trp"
<220> FEATURE:
<221> NAME/KEY: MOD_RES
<222> LOCATION: (6)
<223> OTHER INFORMATION: /product "D-Tryptophan" /label = "D-Trp"
<220> FEATURE:
<221> NAME/KEY: MOD_RES
<222> LOCATION: (7)
<223> OTHER INFORMATION: /product = "Norleueive" /label = "NLE"

<400> SEQUENCE: 40

Xaa Gln Gln Xaa Phe Xaa Trp Xaa
 1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product = "D-Proline" /label = "D-Pro"
<220> FEATURE:
<221> NAME/KEY: MOD_RES
<222> LOCATION: (4)
<223> OTHER INFORMATION: /product = "D-Tryptophan" /label = "D-Trp
<220> FEATURE:
<221> NAME/KEY: MOD_RES
```

```
<222> LOCATION: (6)
<223> OTHER INFORMATION: /product = "D-Tryptophan" /label = "D-Trp"
<220> FEATURE:
<221> NAME/KEY: MOD_RES
<222> LOCATION: (7)
<223> OTHER INFORMATION: /product = "D-Tryptophan" /label = "D-Trp"

<400> SEQUENCE: 41

Xaa Gln Gln Xaa Val Xaa Xaa Met
  1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (2)
<223> OTHER INFORMATION: /product = "D-Tryptophan" /label = "D-Trp"
<220> FEATURE:
<221> NAME/KEY: MOD_RES
<222> LOCATION: (3)
<223> OTHER INFORMATION: /product = "N-Methionine" /label = "N-Me"
<220> FEATURE:
<221> NAME/KEY: MOD_RES
<222> LOCATION: (5)
<223> OTHER INFORMATION: /product = "D-Tryptophan" /label = "D-Trp"

<400> SEQUENCE: 42

Arg Xaa Xaa Phe Xaa Leu Met
  1               5

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (1)
<223> OTHER INFORMATION: /product = "D-arginine" /label = "D-Arg"
<220> FEATURE:
<221> NAME/KEY: MOD_RES
<222> LOCATION: (2)
<223> OTHER INFORMATION: /product = "D-Proline" /label = "D-Pro"
<220> FEATURE:
<221> NAME/KEY: MOD_RES
<222> LOCATION: (9)
<223> OTHER INFORMATION: /product = "D-Histidine" /label = "D-His"

<400> SEQUENCE: 43

Xaa Xaa Lys Pro Gln Gln Xaa Phe Xaa Leu Met
  1               5                  10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (2)
<223> OTHER INFORMATION: /product = "D-Tryptophan" /label = "D-Trp"
<220> FEATURE:
<221> NAME/KEY: MOD_RES
<222> LOCATION: (7)
```

-continued

```
<223> OTHER INFORMATION: /product = "D-Tryptophan" /label = "D-Trp"
<220> FEATURE:
<221> NAME/KEY: MOD_RES
<222> LOCATION: (9)
<223> OTHER INFORMATION: /product = "D-Tryptophan" /label = "D-Trp"

<400> SEQUENCE: 44

Arg Xaa Lys Pro Gln Gln Xaa Phe Xaa Leu Met
 1               5                  10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (1)
<223> OTHER INFORMATION: /product = "D-Arginine" /label = "D-Arg"
<220> FEATURE:
<221> NAME/KEY: MOD_RES
<222> LOCATION: (2)
<223> OTHER INFORMATION: /product = "D-Proline" /label = "D-Pro"
<220> FEATURE:
<221> NAME/KEY: METAL
<222> LOCATION: (7)
<223> OTHER INFORMATION: /product = "D-Tryptophan" /label = "D-Trp
<220> FEATURE:
<221> NAME/KEY: METAL
<222> LOCATION: (9)
<223> OTHER INFORMATION: /product = "D-Tryptophan" /label = "D-Trp

<400> SEQUENCE: 45

Xaa Xaa Lys Pro Gln Gln Xaa Phe Xaa Leu Leu
 1               5                  10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence:  This
      peptide was synthetically generated.
<220> FEATURE:
<221> NAME/KEY: MOD_RES
<222> LOCATION: (1)
<223> OTHER INFORMATION: /product = "D-Arginine" /label = "D-Arg"
<220> FEATURE:
<221> NAME/KEY: MOD_RES
<222> LOCATION: (7)
<223> OTHER INFORMATION: /product = "D-Tryptophan" /label = "D-Trp"
<220> FEATURE:
<221> NAME/KEY: MOD_RES
<222> LOCATION: (9)
<223> OTHER INFORMATION: /product = "D-Tryptophan" /label = "D-Trp"

<400> SEQUENCE: 46

Xaa Pro Lys Pro Gln Gln Xaa Phe Xaa Leu Leu
 1               5                  10
```

DRUG FOR THE TREATMENT OF CANCER

FIELD OF THE INVENTION

The present invention relates to a combination of peptide analogs. The combination may be used to block the uncontrolled multiplication of cancer cells of the colon, rectum, lung, breast, and kidney. The combination may be used to treat cancers of the colon, rectum, lung, breast, and kidney and may be used to treat leukemia and lymphoma. The invention also relates to a pharmaceutical composition containing a combination of such analogs.

BACKGROUND

Reports in the scientific literature disclose that receptors for peptides such as VIP, somatostatin, and bombesin are found on certain tumor cells. The following Table 1 gives a list of tumor cells that secrete and have receptors for VIP, somatostatin, bombesin, and substance P.

TABLE 1

| Peptide | Peptide Secretion And Receptor Positivity | Reference |
|---|---|---|
| VIP | Neuroblastoma | J. Molecular Neurosciences 5(4):231, 1994 |
| | Colorectal and pancreatic adenocarcinoma | N.Eng. J. Med 331(17): 1116, 1994 |
| Somatostatin | Small Cell Lung Cancer | Eur. J. Cancer 31A(2): 184, 1995 |
| | Thyroid carcinoma | Clin. Endocrinol. 42(1): 31, 1995 |
| | Neuroblastoma | Seminars in Oncol. 21: 38, 1994 |
| Bombesin | Small Cell Lung Cancer | Int. J. Cancer 60: 82, 1995 |
| | Glioblastoma | Cancer Res., 54: 5895, 1994 |
| | Pancreatic cancer | Int. J. Pancreatology, 16: 141, 1994 |
| | Gastric cancer | Cancer letters, 85: 111, 1994 |
| | Prostate cancer | Prostate 25(1): 29, 1994 |
| Substance P | Small cell lung cancer | Cancer Research 54(13): 3602–3610 (July 1, 1994) |

SUMMARY OF THE INVENTION

The present invention provides a pharmaceutical composition useful for killing or inhibiting multiplication of tumor cells as well as cancer cells. The pharmaceutical composition may also be useful in preventing, inhibiting, or modulating the hypersecretion of VIP, somatostatin, bombesin, Substance P, or a combination of VIP, somatostatin, bombesin, or Substance P. The composition may suitably comprise, consist of, or consist essentially of a therapeutically effective combination of peptide analogs of somatostatin, VIP, bombesin, and Substance P. The peptide analogs are described in more detail below, but constituents functionally interchangeable with those specifically described may also be employed in the claimed pharmaceutical composition. More particularly, the pharmaceutical composition may suitably comprise, consist of, or consist essentially of an analog of somatostatin and at least four peptides selected from the group consisting of a first analog of VIP, a second analog of VIP, a third analog of VIP, another analog of somatostatin, an analog of bombesin, and an analog of Substance P. More particularly, the composition may suitably comprise, consist of, or consist essentially of a therapeutically effective combination of peptide $SOM_2$ (an analog of somatostatin) and at least four of the following peptides: $VIP_1$ (a VIP antagonist), $VIP_2$ (a VIP receptor binding inhibitor), $VIP_3$ (a VIP receptor antagonist), $SOM_1$ (a somatostatin analog (also abbreviated "CTOP," which is derived from the first letters of the following four amino acids: $Cys^2$, $Tyr^3$, $Orn^5$, and $Pen^5$)), $BOM_1$ (a bombesin antagonist), and $SP_1$ (a Substance P antagonist). In a preferred embodiment, a pharmaceutically acceptable carrier, diluent, or solvent is used. The invention provides a method of treatment for humans, mammals, or other animals suffering from cancer or other tumors. The method may suitably comprise, consist of, or consist essentially of administering a therapeutically effective dose of the pharmaceutical composition so as to kill or inhibit the multiplication of cancer or tumor cells. The method of treatment of the present invention may be particularly useful in the treatment of cancers or tumors of the colon and rectum. The invention also provides a method of treatment for humans, mammals, or other animals suffering from hypersecretion of VIP, somatostatin, bombesin, Substance P, or a combination of VIP, somatostatin, bombesin, or Substance P. The method may suitably comprise, consist of, or consist essentially of administering a therapeutically effective dose of the pharmaceutical composition so as to prevent, inhibit, or modulate the hypersecretion of VIP, somatostatin, bombesin, Substance P, or a combination of VIP, somatostatin, bombesin, or Substance P.

DETAILED DESCRIPTION

Figure 1:
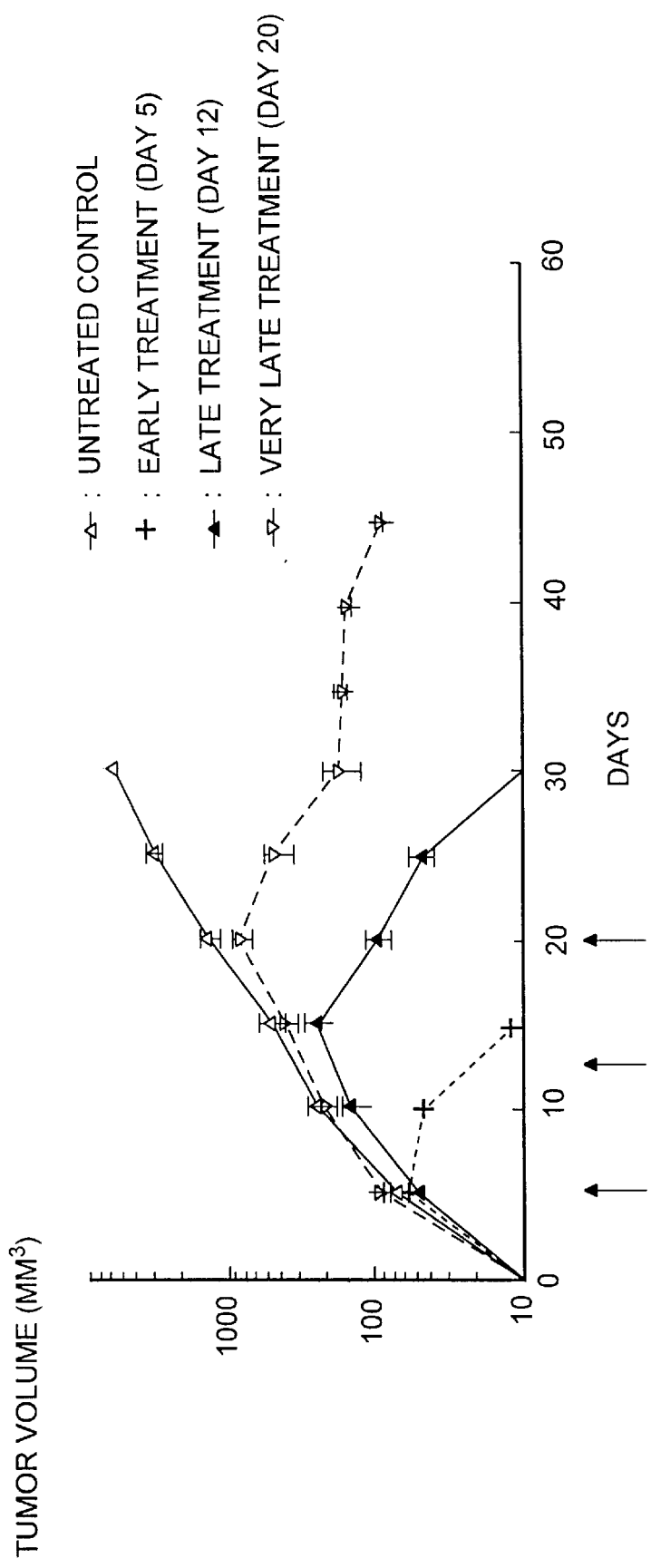
FIG. 1, which shows the effect on tumor regression of treatment onset time with MuJ-7, summarizes the mean tumor volume (in $mm^3$) for all of the mice in the in vivo protocols described in Examples 6–13 versus the day numbers.

We have observed that VIP (vasoactive intestinal peptide), somatostatin, Substance P, and bombesin are secreted by at least some human tumor and cancer cells and that there are binding sites for these peptides on these cells. Specifically, out of a number of peptide growth regulators studied by indirect immunofluorescence, the four peptides (i.e., vasoactive intestinal peptide (VIP), somatostatin, Substance P, and bombesin) were shown to bind to tumor cells. (Herein, the terms "peptide hormones," "growth factors," "peptide growth regulators," and "peptides" each refer to VIP, somatostatin, Substance P, and bombesin.) It may be that there is an autocrine mechanism for cell proliferation where the peptides are secreted by tumor cells and transduce a signal through specific receptors on the same cell type leading to cell proliferation.

As will be described in more detail below, the effects of the analogs of somatostatin, VIP, bombesin, and Substance P on the tumor cell growth and survival were studied using different assay systems. The amino-acid sequences of the seven analogs (VIP$_1$, VIP$_2$, VIP$_3$, SOM$_1$, SOM$_2$, BOM$_1$, and SP$_1$) are given in Table 2. As will be explained in more detail below, the combination of these seven analogs is known as MuJ-7. In the accompanying Sequence Listing section, the amino-acid sequence for VIP$_1$ (a VIP antagonist) is SEQ ID NO:1; and the amino-acid sequence for VIP$_2$ (a VIP receptor binding inhibitor) is SEQ ID NO:2. The analogs were synthesized manually and using a conventional peptide synthesizer. The purity of the peptides was established by performing high performance liquid chromatography and amino acid analysis, while the analysis was reconfirmed on a sequence analyzer.

a novel method of establishing cell lines. The following article, which describes the novel method of establishing cell lines, is incorporated herein by reference: Jaggi, M., Mukherjee, R., "Establishment of Tumorigenic Cell Lines from Biopsies of Human Colon Adenocarcinomas," *Journal of Basic & Applied Biomedicine*, 3(4): 27–35 (1995).

A sandwich ELISA for the peptides was developed and used by the inventors. The following article, which describes the sandwich ELISA, is incorporated herein by reference: Jaggi, M., Mukherjee R., "New, Sensitive and Specific ELISA for the Detection of Neuropeptides in Culture Supernatants," *Journal of Immunoassay*, 15(2): 129–46 (1994). The identity of the peptides was established by reverse phase high performance liquid chromatography and sequence analysis. The binding sites for VIP, somatostatin, Substance P, and bombesin on primary human adenocarcinoma tumor cells of the colon were demonstrated by performing receptor-ligand assays. Two classes of binding sites (high affinity and moderately high affinity) were demonstrated for VIP and somatostatin; a single class of binding site (high affinity) was demonstrated for bombesin; and a single class of binding site (moderately high affinity) was demonstrated for Substance P.

Tables 3, 4, 5, and 6 present data on the receptor affinities for VIP, somatostatin, bombesin, and Substance P on eight different primary tumor cultures of human colon adenocarcinoma. These data were obtained by performing receptor-ligand assays using $^{125}$I-VIP, $^{125}$I-somatostatin, $^{125}$I-bombesin, and $^{125}$I-Substance P. See the section below entitled "Description of Protocols" for a detailed description of the receptor-ligand assay. In Tables 3; 4, 5, and 6, K$_D$(M) represents the dissociation constant, the unit of which is moles (M); and R(M/L) stands for the receptor number (i.e., the number of receptors per tumor cell), the unit of which is moles per liter (M/L). As described in the "Description of Protocols" section below, K$_D$(M) and R(M/L) were com-

TABLE 2

The amino-acid sequences for the seven peptide analogs comprising MuJ-7

| Code | Name | Sequence | SEQ ID NO: |
|---|---|---|---|
| VIP$_1$ | VIP antagonist | Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn-NH$_2$ | SEQ ID NO:1 |
| VIP$_2$ | VIP receptor binding inhibitor | (Leu-Met-Tyr-Pro-Thr-Tyr-Leu-Lys) | SEQ ID NO:2 |
| VIP$_3$ | VIP Receptor Antagonist | (His-Ser-Asp-Ala-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ | SEQ ID NO:11 |
| SOM$_1$ | Somatostatin analog (CTOP) | D-Phe-Cys-Tyr-D-Trp-Orn-Thr-Pen-Thr-NH$_2$ | SEQ ID NO:12 |
| SOM$_2$ | Somatostatin analog | Ala-Gly-Cys-Lys-Asn-Phe-Phe-D-Trp-Lys-Thr-Phe-Thr-Ser-D-Cys(disulfide bridges: 3-14) | SEQ ID NO:13 |
| BOM$_1$ | Bombesin antagonist | D-Phe-Gln-Trp-Ala-Val-Gly-His-Leu-NHEt | SEQ ID NO:14 |
| SP$_1$ | Substance P antagonist | D-Arg-Pro-Lys-Pro-D-Phe-Gln-D-Trp-Leu-Leu-NH$_2$ | SEQ ID NO:15 |

The growth factors synthesized and secreted by tumor cells were identified by different assay systems. For example, the peptide hormones involved in uncontrolled proliferation of cancer cells were identified by performing experiments on established cell lines. The results obtained were complemented with data obtained from experiments conducted on primary tumor cells of human colon adenocarcinoma as a model tissue, for which we have developed puted using LIGAND software, which did Scatchart Analysis using the raw data from the receptor-ligand assays.

A K$_D$(M) value in the range of about $10^{-9}$ to about $10^{-10}$ M indicates a high-affinity receptor, while a K$_D$(M) value in the range of about $10^{-6}$ to about $10^{-8}$ M indicates a receptor with a moderately high affinity. Table 3 shows two K$_D$(M) values and two R(M/L) values for each primary tumor culture because the tumor cells have a high-affinity receptor for VIP as well as a receptor with a moderately high affinity for VIP. Table 4 shows two $K_D(M)$ values and two $R(M/L)$ values for each primary tumor culture because the tumor cells have a high-affinity receptor for somatostatin as well as a receptor with a moderately high affinity for somatostatin. Table 5 shows only one $K_D(M)$ value and one $R(M/L)$ value for each primary tumor culture because the tumor cells appear to have only a high-affinity receptor for bombesin. Table 6 shows only one $K_D(M)$ value and one $R(M/L)$ value for each primary tumor culture because the tumor cells appear to have a receptor with a moderately high affinity for Substance P.

TABLE 3

Dissociation constant ($K_D(M)$) in moles and receptor number ($R(M/L)$) in moles per liter for VIP on eight primary tumor cultures of human colon adenocarcinoma.

| Sample No | $K_D(M)$ | $R(M/L)$ |
|---|---|---|
| PTC-1 | $1.04 \times 10^{-9}$ | $4.83 \times 10^{-11}$ |
|  | $6.33 \times 10^{-7}$ | $1.78 \times 10^{-8}$ |
| PTC-2 | $1.45 \times 10^{-9}$ | $6.23 \times 10^{-11}$ |
|  | $4.23 \times 10^{-7}$ | $1.03 \times 10^{-8}$ |
| PTC-3 | $6.35 \times 10^{-9}$ | $2.45 \times 10^{-10}$ |
|  | $1.51 \times 10^{-6}$ | $2.93 \times 10^{-8}$ |
| PTC-4 | $1.10 \times 10^{-8}$ | $2.75 \times 10^{-10}$ |
|  | $9.45 \times 10^{-7}$ | $5.03 \times 10^{-8}$ |
| PTC-5 | $1.95 \times 10^{-8}$ | $5.29 \times 10^{-10}$ |
|  | $3.51 \times 10^{-6}$ | $8.72 \times 10^{-8}$ |
| PTC-6 | $4.41 \times 10^{-9}$ | $1.05 \times 10^{-10}$ |
|  | $1.88 \times 10^{-6}$ | $3.21 \times 10^{-8}$ |
| PTC-7 | $1.49 \times 10^{-9}$ | $6.12 \times 10^{-11}$ |
|  | $5.55 \times 10^{-7}$ | $9.37 \times 10^{-9}$ |
| PTC-8 | $1.78 \times 10^{-9}$ | $1.50 \times 10^{-10}$ |
|  | $8.42 \times 10^{-6}$ | $8.49 \times 10^{-9}$ |

TABLE 4

Dissociation constant ($K_D(M)$) in moles and receptor number ($R(M/L)$) in moles per liter for somatostatin on eight primary tumor cultures of human colon adenocarcinoma.

| Sample No | $K_D(M)$ | $R(M/L)$ |
|---|---|---|
| PTC-1 | $3.23 \times 10^{-10}$ | $6.01 \times 10^{-11}$ |
|  | $9.37 \times 10^{-8}$ | $4.41 \times 10^{-9}$ |
| PTC-2 | $1.70 \times 10^{-10}$ | $8.99 \times 10^{-11}$ |
|  | $6.35 \times 10^{-8}$ | $2.24 \times 10^{-9}$ |
| PTC-3 | $1.15 \times 10^{-9}$ | $1.06 \times 10^{-10}$ |
|  | $1.34 \times 10^{-7}$ | $5.09 \times 10^{-9}$ |
| PTC-4 | $9.65 \times 10^{-11}$ | $4.66 \times 10^{-11}$ |
|  | $5.64 \times 10^{-8}$ | $2.75 \times 10^{-9}$ |
| PTC-5 | $3.78 \times 10^{-10}$ | $5.82 \times 10^{-11}$ |
|  | $1.54 \times 10^{-8}$ | $1.24 \times 10^{-9}$ |
| PTC-6 | $5.45 \times 10^{-10}$ | $6.85 \times 10^{-11}$ |
|  | $4.30 \times 10^{-8}$ | $1.16 \times 10^{-9}$ |
| PTC-7 | $1.11 \times 10^{-9}$ | $9.81 \times 10^{-11}$ |
|  | $1.28 \times 10^{-7}$ | $3.89 \times 10^{-9}$ |
| PTC-8 | $9.64 \times 10^{-10}$ | $1.74 \times 10^{-10}$ |
|  | $9.92 \times 10^{-8}$ | $6.59 \times 10^{-9}$ |

TABLE 5

Dissociation constant ($K_D(M)$) in moles and receptor number ($R(M/L)$) in moles per liter for bombesin on eight primary tumor cultures of human colon adenocarcinoma.

| Sample No | $K_D(M)$ | $R(M/L)$ |
|---|---|---|
| PTC-1 | $4.39 \times 10^{-10}$ | $2.24 \times 10^{-10}$ |
| PTC-2 | $5.93 \times 10^{-10}$ | $3.22 \times 10^{-10}$ |

TABLE 5-continued

Dissociation constant ($K_D(M)$) in moles and receptor number ($R(M/L)$) in moles per liter for bombesin on eight primary tumor cultures of human colon adenocarcinoma.

| Sample No | $K_D(M)$ | $R(M/L)$ |
|---|---|---|
| PTC-3 | $5.69 \times 10^{-10}$ | $2.97 \times 10^{-10}$ |
| PTC-4 | $5.68 \times 10^{-10}$ | $2.89 \times 10^{-10}$ |
| PTC-5 | $4.62 \times 10^{-10}$ | $3.35 \times 10^{-10}$ |
| PTC-6 | $4.85 \times 10^{-10}$ | $2.24 \times 10^{-10}$ |
| PTC-7 | $6.70 \times 10^{-10}$ | $2.55 \times 10^{-10}$ |
| PTC-8 | $8.83 \times 10^{-10}$ | $2.85 \times 10^{-10}$ |

TABLE 6

Dissociation constant ($K_D(M)$) in moles and receptor number ($R(M/L)$) in moles per liter for Substance P on eight primary tumor cultures of human colon adenocarcinoma.

| Sample No | $K_D(M)$ | $R(M/L)$ |
|---|---|---|
| PTC-1 | $1.54 \times 10^{-7}$ | $1.85 \times 10^{-8}$ |
| PTC-2 | $1.72 \times 10^{-7}$ | $1.71 \times 10^{-8}$ |
| PTC-3 | $1.34 \times 10^{-7}$ | $1.49 \times 10^{-8}$ |
| PTC-4 | $1.54 \times 10^{-7}$ | $1.66 \times 10^{-8}$ |
| PTC-5 | $2.10 \times 10^{-8}$ | $6.2 \times 10^{-9}$ |
| PTC-6 | $2.34 \times 10^{-7}$ | $2.95 \times 10^{-8}$ |
| PTC-7 | $2.62 \times 10^{-8}$ | $7.48 \times 10^{-9}$ |
| PTC-8 | $1.86 \times 10^{-7}$ | $1.32 \times 10^{-8}$ |

An example of a combination within the scope of the invention comprises $SOM_2$, $VIP_1$, $VIP_2$, $VIP_3$, $SOM_1$, $BOM_1$, and $SP_1$. A combination, hereinafter referred to as MuJ-7, was prepared using the following seven peptide analogs: (1) $VIP_1$ (the VIP antagonist) having a molecular weight of approximately 3464.9 and a concentration of approximately $10^{-7}M$; (2) $VIP_2$ (the VIP receptor binding inhibitor) having a molecular weight of approximately 1027.55 and a concentration of approximately $10^{-8}M$; (3) $VIP_3$ (the VIP receptor antagonist) having a molecular weight of approximately 3342.09 and a concentration of approximately $10^{-8}M$; (4) $SOM_1$, (the somatostatin analog (CTOP)) having a molecular weight of approximately 1061.59 and a concentration of approximately $10^{-9}M$; (5) $SOM_2$ (the analog of somatostatin) having a molecular weight of approximately 1637.9 and a concentration of approximately $10^{-8}M$; (6) $BOM_1$ (the bombesin antagonist) having a molecular weight of approximately 983.55 and a concentration of approximately $10^{-8}M$; and (7) $SP_1$ (the Substance P antagonist) having a molecular weight of approximately 1515.83 and a concentration of approximately $10^{-8}M$. The preceding sentence sets forth the preferred concentrations of the seven analogs comprising MuJ-7. Nevertheless, it is expected that MuJ-7 would be effective if the concentration of each of the seven analogs ranged from approximately $10^{-6}M$ to approximately $10^{-12}M$.

MuJ-7 may be prepared in the following way. A stock solution of each of the seven peptide analogs is prepared with a pH of approximately 7.0 to approximately 7.4. Although sterile phosphate buffered saline was used to prepare the stock solutions for the testing described below, other diluents may be used such as RPMI 1640, buffered saline, isotonic NaCl, Ringer's solution, water (for injection), distilled water, polyethylene glycol (neat or in water), 2% Tween in water, dimethylsulfoxide to 50% in water, propylene glycol (neat or in water), balanced salt solution, glycerol, and other conventional fluids that are suitable for intravenous administration. To obtain a pH in the range of approximately 7.0 to approximately 7.4 for each stock solution, the pH can be adjusted by using 1N HCl for the lowering the pH or 1N NaOH for raising the pH, although other conventional agents for adjusting the pH can be used. The concentration of the peptide analog in each stock solution is approximately $10^{-3}$M. Aliquots of the seven peptides analogs are mixed together such that the MuJ-7 formulation contains approximately equal weights of each of the seven peptide analogs. In MuJ-7, the concentration of $VIP_1$ is approximately $10^{-7}$M; the concentration of $VIP_2$ is approximately $10^{-8}$M; the concentration of $VIP_3$ is approximately $10^{-8}$M; the concentration of $SOM_1$ is approximately $10^{-9}$M; the concentration of $SOM_2$ is approximately $10^{-8}$M; the concentration of $BOM_1$ is approximately $10^{-8}$M; and the concentration of $SP_1$ is approximately $10^{-8}$M. In one exemplary embodiment, the pH of the MuJ-7 solution may range from approximately 7.0 to approximately 7.4. To obtain a pH in this range, the pH can be adjusted by using 1 N HCl for lowering the pH or 1 N NaOH for raising the pH, although other conventional agents for adjusting the pH can be used.

MuJ-7 was tested against primary tumor cells of human colon adenocarcinoma, and each of the peptide analogs comprising MuJ-7 was tested individually against human colon adenocarcinoma tumor cells and other cancer cell lines. The results for primary tumor cells of human colon adenocarcinoma are summarized in Table 7; and the results for other tumor or cancer cell lines are summarized in Table 8. Tables 7 and 8 list the maximum cytotoxicity achieved for each peptide analog and MuJ-7.

The cytotoxicity of MuJ-7 and each of the peptide analogs listed in Tables 7 and 8 was tested by performing a one-day MTT cytotoxicity assay, which is based on the principle of uptake of MTT (3- (4, 5-dimethylthiazol-2-yl)-2,5-diphenyl tetrazolium bromide), a tetrazolium salt, by the metabolically active cells where it is metabolized by active mitochondria into a blue-colored formazan product, which can be read spectrophotometrically. The following article, which describes the MTT assay, is incorporated herein by reference: Mosmann, T., "Rapid Colorimetric Assay for Cellular Growth and Survival: Application to Proliferation and Cytotoxicity Assays", *Journal of Immunological Methods* 65: 55–63 (1983). To prepare the MTT stock solution needed for the one-day MTT cytotoxic assay, MTT (3-(4,5-dimethylthiazol-2-yl)-2, 5-diphenyl tetrazolium bromide) (Sigma catalogue number M 2128) was dissolved in phosphate buffered saline with a pH of 7.4 to obtain an MTT concentration of 5 mg/ml; the resulting mixture was filtered through a 0.22 µ filter to sterilize and remove a small amount of insoluble residue; the filtered mixture was the MTT stock solution (20 µl per 200 µl of medium). Briefly, for each type of tumor cell, approximately 20,000–50,000 cells were seeded in a 96-well culture plate and incubated with each of the peptide analogs or MuJ-7 in a $CO_2$ incubator for approximately 24 hours. The concentrations of the peptide analogs and MuJ-7 are given in Tables 7 and 8. (In Table 8, the concentrations of the peptide analogs include $10^{-6}$M, $10^{-7}$M, and $10^{-8}$M.) Controls, which were not treated with the peptide analogs or MuJ-7, were similarly incubated. The assay was terminated after approximately 24 hours by adding approximately mately 100 µg (20 µl) of MTT to each well, then incubating for approximately one additional hour, and finally adding approximately 50 µl of 10% SDS-0.01 N HCl to each well to lyse the cells and dissolve the formazan. After incubating for approximately one hour at 37° C., the plate was read spectrophotometrically at 540 nm; and the cytotoxicity percentage (i.e., the killing percentage or the inhibition percentage) was calculated using the following formula:

Cytotoxicity percentage=$100 \times [1-(X/R_1)]$, where X=(absorbance of the treated sample at 540 nm)–(absorbance of a blank at 540 nm), and $R_1$=(absorbance of the untreated control at 540 nm)–(absorbance of a blank at 540 nm). Thus, in each of the MTT cytotoxicity assays reported herein, the cytotoxicity percentage was calculated according to the above formula and was based on the proliferation of the untreated controls, the value of which was taken as 100%.

TABLE 7

Cytotoxic effect of individual peptide analogs and MuJ-7 on primary tumor cells of human colon adenocarcinoma

| Peptide Analog | Concentration | % Killing |
|---|---|---|
| $VIP_1$ | $10^{-7}$ M | 61 |
| $VIP_2$ | $10^{-8}$ M | 77 |
| $VIP_3$ | $10^{-8}$ M | 76 |
| $SOM_1$ | $10^{-9}$ M | 73 |
| $SOM_2$ | $10^{-8}$ M | 79 |
| $BOM_1$ | $10^{-8}$ M | 64 |
| $SP_1$ | $10^{-8}$ M | 54 |
| MuJ-7 | $VIP_1(10^{-7}$ M$) + VIP_2 (10^{-8}$M$) + VIP_3(10^{-8}$ M$) + SOM_1(10^{-9}$M$) + SOM_2(10^{-8}$M$) + BOM_1 (10^{-8}$M$) + SP_1(10^{8}$ M$)$ | 94 |

TABLE 8

Cytotoxic effect of individual peptide analogs on cell lines (percent inhibition)

Percent cytotoxicity on treatment with analogs at concentration

| Cell line | $VIP_1$(10M) | | | $VIP_2$(10M) | | | $VIP_3$(10M) | | | $SOM_1$(10M) | | | $SOM_2$(10M) | | | $BOM_1$(10M) | | | $SP_1$(10M) | | |
|---|---|---|---|---|---|---|---|---|---|---|---|---|---|---|---|---|---|---|---|---|---|
| | −6 | −7 | −8 | −6 | −7 | −8 | −6 | −7 | −8 | −6 | −7 | −8 | −6 | −7 | −8 | −6 | −7 | −8 | −6 | −7 | −8 |
| K562 | — | 10 | 19 | 13 | 11 | 2 | 18 | 37 | 29 | 34 | 33 | 9 | 9 | 14 | 27 | 19 | 14 | 1 | | | |
| MOLT-4 | 5 | 32 | 21 | 10 | 11 | — | 7 | 31 | 33 | 23 | 44 | 11 | — | 23 | 39 | 25 | 16 | 5 | | | |
| L132 | — | 10 | 13 | 10 | 32 | 43 | 23 | 26 | 1 | 36 | 40 | 22 | 11 | 32 | 37 | 33 | 33 | 16 | 22 | | |
| PC3 | 16 | 30 | 33 | 32 | 27 | 16 | 7 | 21 | 21 | 24 | 19 | 6 | 2 | 14 | 21 | 23 | 22 | 9 | | | |
| MCF-7 | 12 | 5 | 15 | 17 | 12 | 40 | 4 | — | 2 | — | — | 11 | — | — | 18 | — | 2 | 7 | | | |
| HuTu80 | — | — | — | — | — | — | — | — | — | — | — | — | — | — | 2 | — | — | — | — | — | — |
| Hu746T | 11 | 36 | 25 | 13 | 17 | 20 | 20 | — | 9 | 31 | 40 | 34 | 18 | 29 | 27 | 5 | 32 | 31 | 19 | 15 | 7 |
| SKO.007 | — | — | — | — | — | — | — | — | — | 2 | — | — | — | — | — | — | — | — | — | — | — |

TABLE 8-continued

Cytotoxic effect of individual peptide analogs on cell lines (percent inhibition)

Percent cytotoxicity on treatment with analogs at concentration

| Cell line | $VIP_1(10M)$ | | | $VIP_2(10M)$ | | | $VIP_3(10M)$ | | | $SOM_1(10M)$ | | | $SOM_2(10M)$ | | | $BOM_1(10M)$ | | | $SP_1(10M)$ | | |
|---|---|---|---|---|---|---|---|---|---|---|---|---|---|---|---|---|---|---|---|---|---|
| | −6 | −7 | −8 | −6 | −7 | −8 | −6 | −7 | −8 | −6 | −7 | −8 | −6 | −7 | −8 | −6 | −7 | −8 | −6 | −7 | −8 |
| HT29 | — | 1 | 9 | 49 | 10 | 9 | 22 | 57 | — | — | — | 17 | — | — | — | 32 | — | — | 3 | 27 | — |
| SW620 | 9 | 6 | 4 | 10 | 10 | 6 | — | 9 | 16 | 5 | 9 | 11 | 9 | 10 | 1 | — | 4 | 6 | 8 | 4 | 10 |
| G401 | — | — | — | — | — | — | — | — | — | — | — | — | — | — | — | — | — | — | — | — | — |
| SK.MEL.28 | — | — | — | — | — | — | — | — | — | — | — | — | — | — | — | — | — | — | — | — | — |
| PTC(Colon) | 43 | 58 | 61 | 58 | 76 | 77 | 42 | 58 | 76 | 41 | 56 | 72 | 58 | 62 | 79 | 44 | 60 | 64 | — | — | — |

In Table 8, K562 cells are human leukemia cells; MOLT-4 cells are human lymphoma cells; L 132 cells are human lung carcinoma cells; PC3 cells are human pancreas tumor cells; MCF-7 cells are human breast tumor cells; HuTu80 cells are human duodenum tumor cells; Hu 746T cells are human stomach tumor cells; SKO.007 cells are human myeloma cells; HT29 cells are human colon tumor cells; SW 620 cells are human colon tumor cells; G 401 cells are human kidney tumor cells; SK.MEL.28 cells are human melanoma cells; and PTC cells are human colon tumor cells.

The results in Tables 7 and 8 indicate that the peptide analogs ($VIP_1$, $VIP_2$, $VIP_3$, $SOM_1$, $SOM_2$, $BOM_1$, and $SP_1$) are more effective when used in the MuJ-7 combination.

Five different subcombinations of the seven peptide analogs comprising MuJ-7 were tested against human colon adenocarcinoma tumor cells. The subcombinations are listed in Table 9. Each subcombination was tested by performing a one-day MTT cytotoxicity assay. Briefly, approximately 20,000–50,000 primary tumor cells of human colon adenocarcinoma were seeded in a 96-well culture plate and incubated with each subcombination in a $CO_2$ incubator for approximately 24 hours. The concentrations of the peptide analogs in each subcombination are given in Table 9. Controls, which were not treated with the subcombinations, were similarly incubated. The assay was terminated after approximately 24 hours by adding approximately 100 μg (20 μl) of MTT to each well, then incubating for approximately one additional hour, and finally adding approximately 50 μl of 10% SDS-0.01 N HCl to each well to lyse the cells and dissolve the formazan. After incubating for approximately one hour at 37° C., the plate was read spectrophotometrically at 540 nm; and the cytotoxicity percentage (i.e., the killing percentage) was calculated using the formula presented above. Table 9 lists the maximum cytotoxicity achieved for each subcombination.

TABLE 9

Cytotoxicity of subcombinations of peptide analogs on primary tumor cells of human colon adenocarcinoma.

| Subcombination Number | Subcombination | Killing percentage (approximate) |
|---|---|---|
| 1 | $VIP_1(10^7M) + SOM_1(10^{-9}M) + BOM_1(10^{-8}M)$ | 64.7 |
| 2 | $VIP_1(10^{-7}M) + VIP_2(10^{-8}M) + SOM_1(10^{-9}M) + BOM_1(10^{-8}M)$ | 75.3 |

TABLE 9-continued

Cytotoxicity of subcombinations of peptide analogs on primary tumor cells of human colon adenocarcinoma.

| Subcombination Number | Subcombination | Killing percentage (approximate) |
|---|---|---|
| 3 | $VIP_1(10^{-7}M) + VIP_2(10^{-8}M) + SOM_1(10^{-9}M) + SOM_2(10^{-8}M) + SP_1(10^{-8}M)$ | 82.9 |
| 4 | $VIP_1(10^{-7}M) + VIP_2(10^{-8}M) + VIP_3(10^{-8}M) + SOM_1(10^{-9}M) + SOM_2(10^{-8}M) + BOM_1(10^{-8}M)$ | 90.2 |
| 5 | $VIP_1(10^{-7}M) + VIP_2(10^{-8}M) + SOM_1(10^{-9}M) + SOM_2(10^{-8}M) + BOM_1(10^{-8}M)$ | 94.9 |

In another experiment, these other peptide analogs were tested: somatostatin analog—RC-160; Substance P analogs—Substance $P_{1-6}$ and Spantide I; cholecystokinin analog—CCK-33; and glucagon analog—human glucagon. Each of these peptide analogs was tested against primary tumor cells of human colon adenocarcinoma. Each peptide analog was tested at concentrations between $10^{-6}M$ and $10^{-10}M$ performing a one-day MTT cytotoxicity assay. Briefly, approximately 20,000–50,000 primary tumor cells of human colon adenocarcinoma were seeded in a 96-well culture plate and incubated with each peptide analog in a $CO_2$ incubator for approximately 24 hours. Controls, which were not treated with the peptide analogs, were similarly incubated. The assay was terminated after approximately 24 hours by adding approximately 100 μg (20 μl) of MTT to each well, then incubating for approximately one additional hour, and finally adding approximately 50 μl of 10% SDS-0.01N HCl to each well to lyse the cells and dissolve the formazan. After incubating for approximately one hour at 37° C., the plate was read spectrophotometrically at 540 nm; and the cytotoxicity percentage (i.e., inhibition percentage) was calculated using the formula presented above. The maximum cytotoxicity achieved for Substance $P_{1-6}$ was approximately 35.9%; the maximum cytotoxicity achieved for RC-160 was approximately 58.0%; the maximum cytotoxicity achieved for Spantide I was approximately 30.8%; the maximum cytotoxicity achieved for human glucagon was approximately 0%; and the maximum cytotoxicity achieved for CCK-33 was approximately 17.8%.

Table 10 lists other VIP analogs; Table 11 lists other somatostatin statin analogs; Table 12 lists other bombesin analogs; and Table 13 lists other Substance P analogs. The analogs listed in Tables 10–13 may be able to replace some of the peptide analogs comprising MuJ-7.

In Tables 2 and 10–13 and in the Sequence Listing, "Pen" represents penicillamine; "Ψ" represents a surrogate bond; "®" represents a reduced bond; "pGlu" represents pyroglutamic acid (i.e., 5-oxo-proline); "NicLys" represents lysine-(Nicotinoyl) (i.e., nicotine attached to the ε amino group of the lysine side chain); "MePhec" represents methylphenylalanine; and "Nle" represents norleucine.

The amino-acid sequences disclosed in Tables 2 and 10–13 and claimed herein may include conservatively modified variants of the amino-acid sequences disclosed in Tables 2 and 10–13. It is believed that the claimed invention would still be effective if the amino-acid sequences disclosed in Tables 2 and 10–13 were shortened by removing amino-acid residues (e.g., one, two, or perhaps more amino-acid residues) from the C-terminus and/or from the N-terminus. It is also believed that the claimed invention would still be effective if the amino-acid residues (e.g., one, two, or perhaps more amino-acid residues) at the C-terminus and/or at the N-terminus of the amino-acid sequences disclosed in Tables 2 and 10–13 were replaced with different amino-acid residues.

TABLE 10

VIP analogs

| S.No | Name | Sequence | SEQ ID NO: |
|---|---|---|---|
| 1 | VIP 10-28 | Tyr-Thr-Arg-Leu-Arg-Lys-Gln-Met-Ala-Val-Lys-Lys-Tyr-Leu-Asn-Ser-Ile-Leu-Asn-NH$_2$ | SEQ ID NO:3 |
| 2 | VIP Antagonist ([Ac-Tyr$^1$,D-Phe$^2$]-Growth Hormone Releasing Factor 1-29 Amide | Ac-Tyr-D-Phe-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-NH$_2$ | SEQ ID NO:16 |
| 3 | VIP (6-28) | Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn-NH$_2$ | SEQ ID NO:4 |

TABLE 11

Somatostatin analogs

| S.No | Name | Sequence | SEQ ID NO: |
|---|---|---|---|
| 1 | [D-Trp$^8$]-Somatostatin | Ala-Gly-Cys-Lys-Asn-Phe-Phe-D-Trp-Lys-Thr-Phe-Thr-Ser-Cys | SEQ ID NO:17 |
| 2 | CTAP | D-Phe-Cys-Tyr-D-Trp-Arg-Thr-Pen-Thr-NH$_2$ | SEQ ID NO:18 |
| 3 | Somatostatin agonist | β-(2-Naphthyl)-D-Ala-Cys-Tyr-D-Trp-Lys-Val-Cys-Thr-NH$_2$ | SEQ ID NO:19 |
| 4 | Somatostatin analog | D-Phe-Cys-Tyr-D-Trp-Lys-Cys-Thr-NH$_2$ | SEQ ID NO:20 |
| 5 | Leu$^8$,D-Trp$^{22}$,Tyr$^{25}$]-Somatostatin 28 | Ser-Ala-Asn-Ser-Asn-Pro-Ala-Leu-Ala-Pro-Arg-Glu-Arg-Lys-Ala-Gly-Cys-Lys-Asn-Phe-Phe-D-Trp-Lys-Thr-Tyr-Thr-Ser-Cys | SEQ ID NO:21 |
| 6 | [D-Trp$^8$,Tyr$^{11}$]-Somatostatin | Ala-Gly-Cys-Lys-Asn-Phe-Phe-D-Trp-Lys-Thr-Tyr-Thr-Ser-Cys | SEQ ID NO:22 |
| 7 | [D-Trp-$^{11}$]-Somatostatin | Ala-Gly-Cys-Lys-Asn-Phe-Phe-Trp-Lys-Thr-D-Trp-Thr-Ser-Cys | SEQ ID NO:23 |
| 8 | [Tyr$^1$]-Somatostatin | Tyr-Gly-Cys-Lys-Asn-Phe-Phe-Trp-Lys-Thr-Phe-Thr-Ser-Cys | SEQ ID NO:5 |
| 9 | [Tyr$^{11}$]-Somatostatin | Ala-Gly-Cys-Lys-Asn-Phe-Phe-Trp-Lys-Thr-Tyr-Thr-Ser-Cys | SEQ ID NO:6 |

TABLE 11-continued

Somatostatin analogs

| S.No | Name | Sequence | SEQ ID NO: |
|---|---|---|---|
| 10 | Somatostatin analog | β-(2-naphthyl)-D-Ala-Cys-Tyr-D-Trp-Lys-Val-Cys-Thr-NH$_2$ | SEQ ID NO:24 |
| 11 | [Des-Ala$^1$,Des-Gly$^2$,His$^{4,5}$,D-Trp$^8$]-Somatostatin | Cys-His-His-Phe-Phe-D-Trp-Lys-Thr-Phe-Thr-Ser-Cys | SEQ ID NO:25 |

TABLE 12

Bombesin analogs

| S.No | Name | Sequence | SEQ ID NO: |
|---|---|---|---|
| 1 | [Leu$^{13}$-ψCH$_2$NH)Leu$^{14}$]-Bombesin | pGlu-Gln-Arg-Leu-Gly-Asn-Gln-Trp-Ala-Val-Gly-His-Leu-ψ(CH$_2$NH)Leu-NH$_2$ | SEQ ID NO:7 |
| 2 | [D-Arg$^1$,D-Pro$^2$,D-Trp$^{7,9}$,Leu$^{11}$]-Substance P | D-Arg-D-Pro-Lys-Pro-Gln-Gln-D-Trp-Phe-D-Trp-Leu-Leu-NH$_2$ | SEQ ID NO:26 |
| 3 | (Leu$^{13}$-®-Leu$^{14}$)-Bombesin | Pyr-Gln-Arg-Leu-Gly-Asn-Gln-Trp-Ala-Val-Gly-His-Leu-(®)-Leu-NH$_2$ | SEQ ID NO:8 |
| 4 | (D-Phe$^{12}$,Leu$^{14}$)-Bombesin | Pry-Gln-Arg-Leu-Gly-Asn-Gln-Trp-Ala-Val-Gly-D-Phe-Leu-Leu-NH$_2$ | SEQ ID NO:27 |
| 5 | (Tyr$^4$,D-Phe$^{12}$)-Bombesin | pGlu-Gln-Arg-Tyr-Gly-Asn-Gln-Trp-Ala-Val-Gly-D-Phe-Leu-Met-NH$_2$ | SEQ ID NO:28 |
| 6 | [D-Phe$^{12}$]-Bombesin (Bombesin Receptor Antagonist) | pGlu-Gln-Arg-Leu-Gly-Asn-Gln-Trp-Ala-Val-Gly-D-Phe-Leu-Met-NH$_2$ | SEQ ID NO:29 |
| 7 | [deamino-Phe$^6$,His$^7$,D-Ala$^{11}$,D-Pro$^{13}$-ψ(CH$_2$NH)-Phe$^{14}$]-Bombesin fragment 6-14 | Deamino-Phe-His-Trp-Ala-Val-D-Ala-His-D-Pro-ψ[CH$_2$NH]-Phe-NH$_2$ | SEQ ID NO:30 |
| 8 | Bombesin fragment 8-14 | Trp-Ala-Val-Gly-His-Leu-Met-NH$_2$ | SEQ ID NO:9 |
| 9 | (Tyr$^4$)-Bombersin | pGlu-Gln-Arg-Tyr-Gly-Asn-Gln-Trp-Ala-Val-Gly-His-Leu-Met-NH$_2$ | SEQ ID NO:10 |

TABLE 13

Substance P analogs

| S.No | Name | Sequence | SEQ ID NO: |
|---|---|---|---|
| 1 | Spantide 1 ([D-Arg$^1$,D-Trp$^{7,9}$,Leu$^{11}$]-Substance P) | D-Arg-Pro-Lys-Pro-Gln-Gln-D-Trp-Phe-D-Trp-Leu-Leu-NH$_2$ | SEQ ID NO:31 |
| 2 | Spantide II | D-NicLys-Pro-Thr-Pal-Pro-D-Cl$_2$Phe-Asn-D-Trp-Phe-D-Trp-Leu-Nle-NH$_2$ | SEQ ID NO:32 |
| 3 | [D-Pro$^2$,D-Phe$^7$,D-Trp$^9$]-Substance P | Arg-D-Pro-Lys-Pro-Gln-Gln-D-Phe-Phe-D-Trp-Leu-Met-NH$_2$ | SEQ ID NO:33 |
| 4 | [D-Pro$^2$,D-Trp$^{7,9}$]-Substance P | Arg-D-Pro-Lys-Pro-Gln-Gln-D-Trp-Phe-D-Trp-Leu-Met-NH$_2$ | SEQ ID NO:34 |
| 5 | [D-Pro$^4$,D-Trp$^{7,9}$]-Substance P 4-11 | D-Pro-Gln-Gln-D-Trp-Phe-D-Trp-Leu-Met-NH$_2$ | SEQ ID NO:35 |

TABLE 13-continued

Substance P analogs

| S.No | Name | Sequence | |
|---|---|---|---|
| 6 | [Arg$^6$,D-Trp$^{7,9}$,MePhe$^8$]-Substance P 6-11 | Arg-D-Trp-MePhe-D-Trp-Leu-Met-NH$_2$ | SEQ ID NO:36 |
| 7 | (D-Arg$^1$,D-Phe$^5$,D-Trp$^{7,9}$,Leu$^{11}$)-Substance P | D-Arg-Pro-Lys-Pro-D-Phe-Gln-D-Trp-Phe-D-Trp-Leu-Leu-NH$_2$ | SEQ ID NO:37 |
| 8 | [D-Pro$^4$,D-Trp$^{7,9,10}$,Phe$^{11}$]-Substance P 4-11 | D-Pro-Gln-Gln-D-Trp-Phe-D-Trp-D-Trp-Phe-NH$_2$ | SEQ ID NO:38 |
| 9 | [D-Pro$^4$,D-Trp$^{7,9,10}$]-Substance P 4-11 | D-Pro-Gln-Gln-D-Trp-Phe-D-Trp-D-Trp-Met-NH$_2$ | SEQ ID NO:39 |
| 10 | (D-Pro$^4$,D-Trp$^{7,9}$,Nle$^{11}$)-Substance P (4-11) | D-Pro-Gln-Gln-D-Trp-Phe-D-Trp-Trp-Nle-NH$_2$ | SEQ ID NO:40 |
| 11 | (D-Pro$^4$,D-Trp$^{7,9,10}$,Val$^8$)-Substance P (4-11) | D-Pro-Gln-Gln-D-Trp-Val-D-Trp-D-Trp-Met-NH$_2$ | SEQ ID NO:41 |
| 12 | (Arg$^6$,D-Trp$^{7,9}$,N-Me-Phe$^8$)-Substance P (6-11) | Arg-D-Trp-N-Me-Phe-D-Trp-Leu-Met-NH$_2$ | SEQ ID NO:42 |
| 13 | [D-Arg$^1$,D-Pro$^2$,D-Phe$^7$,D-His$^9$]-Substance P | D-Arg-D-Pro-Lys-Pro-Gln-Gln-D-Phe-Phe-D-His-Leu-Met-NH$_2$ | SEQ ID NO:43 |
| 14 | [D-Trp$^{2,7,9}$]-Substance P | Arg-D-Trp-Lys-Pro-Gln-Gln-D-Trp-Phe-D-Trp-Leu-Met-NH$_2$ | SEQ ID NO:44 |
| 15 | [D-Arg$^1$,D-Pro$^2$,D-Trp$^{7,9}$,Leu$^{11}$]-Substance P | D-Arg-D-Pro-Lys-Pro-Gln-Gln-D-Trp-Phe-D-Trp-Leu-Leu-NH$_2$ | SEQ ID NO:45 |
| 16 | [D-Arg$^1$,D-Trp$^{7,9}$,Leu$^{11}$]-Substance P | D-Arg-Pro-Lys-Pro-Gln-Gln-D-Trp-Phe-D-Trp-Leu-Leu-NH$_2$ | SEQ ID NO:46 |

Another aspect of the invention provides a method for treating a mammal (including a human being) afflicted with cancer. The types of cancer that may be treated include, but are not necessarily limited to, leukemia and lymphoma; adenocarcinoma of the stomach, pancreas, and prostate; and cancer of the colon, rectum, lung, breast, and kidney. In addition, it is expected that the invention will provide a method for treating other diseases and cancers characterized by hypersecretion of one or more of the peptides VIP, somatostatin, bombesin, and Substance P.

The methods of this invention comprise, consist of, or consist essentially of: administering systematically to the mammal a therapeutically effective combination of peptide SOM$_2$ and at least four of peptides: VIP$_1$, VIP$_2$, VIP$_3$, SOM$_1$, BOM$_1$, and SP$_1$. An effective dose of the combination ranges from 15 to 170 µg (preferably 25 to 40 µg) of the peptides per kg of the body weight of the mammal, with the dose dependent on the effects sought, the manner of administration, the peptides selected, and the cancer being treated. Systemic administration refers to oral, rectal, nasal, transdermal, and parenteral (i.e., intramuscular, intravenous, and subcutaneous). In accordance with good clinical practice, it is preferred to administer the composition at a dose that will produce anticancer effects without causing undue harmful side effects. The composition may be administered either alone or as a mixture with other therapeutic agents.

The composition may optionally and preferably contain pharmaceutically acceptable diluents, excipients, solvents, binders, stabilizers, and the like. Such diluents may include: RPMI 1640, buffered saline, isotonic NaCl, Ringer's solution, water, distilled water, polyethylene glycol (neat or in water), 2% tween in water, dimethylsulfoxide to 50% in water, propylene glycol (neat or in water), phosphate buffered saline, balanced salt solution, glycerol, and other conventional fluids that are suitable for intravenous administration. Pharmaceutical compositions which provide from about 10 to 2000 µg of the composition per unit dose are preferred and are conventionally prepared as tablets, lozenges, capsules, powders, aqueous or oily suspensions, syrups, elixirs, and aqueous solutions. The nature of the pharmaceutical composition employed will, of course, depend on the desired route of administration.

The present invention is further described in detail with reference to the following examples, which are given for the purpose of merely illustrating the invention without limiting it.

In Vitro Studies of MuJ-7:

EXAMPLE 1

A primary tumor cell line of human colon adenocarcinoma was established by using fine needle aspiration cytology (FNAC) and histopathology confirmed tumor tissue of human colon adenocarcinoma. These cells stained positive with a monoclonal antibody specific for a 91 KD surface antigen present on human colon adenocarcinoma cells. The tumorigenicity of these cells was demonstrated by the ability of these cells to form tumors in nude mice on subcutaneous injection. The characteristics of the 12 primary cultures are given in Table 14.

TABLE 14

Characteristic features of human colon adenocarcinoma biopsies cultured in vitro. Note that cultures established from all the tumor biopsies were then xenografted in nude mice.

| B.No | Age | Sex | Site | FNAC | Hist. | MAb | Pass. No | Soft Agar | Tumor induction |
|------|-----|-----|------|------|-------|-----|----------|-----------|-----------------|
| 1 | 52 | M | AC | + | + | + | 36 | + | + |
| 2 | 47 | F | DC | + | + | + | 36 | + | + |
| 3 | 74 | F | DC | + | + | + | 34 | + | + |
| 4 | 68 | M | TC | + | + | + | 32 | + | + |
| 5 | 60 | M | DC | + | + | + | 32 | + | + |
| 6 | 58 | M | AC | ND | + | + | 29 | + | + |
| 7 | 71 | F | DC | + | ND | + | 28 | + | + |
| 8 | 69 | M | AC | ND | + | + | 18 | + | + |
| 9 | 57 | M | TC | + | ND | + | 14 | + | + |
| 10 | 73 | F | DC | + | + | + | 09 | + | + |
| 11 | 50 | M | AC | ND | + | + | 06 | + | + |
| 12 | 69 | M | AC | + | + | + | 06 | + | + |

B.No: Biopsy number;
M: Male;
F: Female;
AC: Ascending colon;
DC: Descending colon;
TC: Transverse colon;
FNAC: Fine Needle Aspiration Cytology;
Hist.: Histopathology;
Mab: Monoclonal Antibody Marker;
Pass No.: Passage number;
ND: Not done The anti-proliferative effects of MuJ-7 were studied in a 96-well culture plate, wherein the human colon adenocarcinoma tumor cells (approximately 50,000 cells per well) from the each of the twelve human colon adenocarcinoma cell cultures listed in Table 14 were incubated in a $CO_2$ incubator at approximately 37° C. for approximately 72 hours with MuJ-7 (approximately 20 µl of MuJ-7 per well). Human colon adenocarcinoma cells not treated with MuJ-7 served as controls. Tritiated [$^3$H] thymidine (approximately 1 µCi per well) was added to each well, and the plate was incubated for approximately 1 additional hour. The cells were harvested on filter mats, and incorporation of [$^3$H] thymidine into the dividing cells was counted on a Beta plate (Pharmacia). For each of the tritiated [$^3$H] thymidine cytotoxicity assays described herein, the proliferation of cells in the untreated controls was taken as 100%. In Example 1, it was observed that MuJ-7 inhibited proliferation of the tumor cells by approximately 95%.

EXAMPLE 2

The cytotoxic effect of MuJ-7 was reconfirmed by a one-day MTT assay. The method for preparing the MTT stock solution for the one-day MTT cytotoxic assay was described above. Briefly, the 12 human colon adenocarcinoma tumor cell cultures, which were described above in Table 14, were incubated in a 96-well culture plate with MuJ-7 (approximately 20 µl of MuJ-7 were added per well at time=0 hours) for approximately 24 hours at approximately 37° C. in approximately 5% $CO_2$. The controls were cells from the 12 human colon adenocarcinoma cell cultures that were not treated with MuJ-7. Then, stock MTT solution (approximately 100 µg of MTT per well) was added to each well, and incubation continued for approximately 1 additional hour. The formazan crystals that formed inside the cells were dissolved with a detergent comprising approximately 10% sodium dodecyl sulfate and approximately 0.01 N HCl; and the optical density of each well was read spectrophotometrically at 540 nm. The optical density was directly proportional to the number of proliferating and metabolically active cells. MuJ-7 inhibited proliferationviability in each of the 12 human colon adenocarcinoma cell cultures as assessed by the MTT cytotoxic assay. The inhibition percentage ranged from approximately 80.7% to approximately 95.2%. Table 15 lists the approximate inhibition percentages for each of the 12 human colon adenocarcinoma cell lines. Biopsy numbers 1 through 12 in Table 14 correspond respectively to sample numbers PTC-1 through PTC-12 in Table 15.

TABLE 15

Inhibition percentages for each of the 12 human colon adenocarcinoma cell lines

| Sample No. | Percent Inhibition |
|------------|--------------------|
| PTC-1 | 95.2 |
| PTC-2 | 89.1 |
| PTC-3 | 94.6 |
| PTC-4 | 82.2 |
| PTC-5 | 74.2 |
| PTC-6 | 81.6 |
| PTC-7 | 93.8 |
| PTC-8 | 94.9 |
| PTC-9 | 81.5 |
| PTC-10 | 82.7 |
| PTC-11 | 84.6 |
| PTC-12 | 80.7 |

EXAMPLE 3

The cytotoxic effect of MuJ-7 was tested using a three-day MTT cytotoxic assay on three human colon cancer cell lines: CoLo 205, HT 29, and SW 620. The method for preparing the MTT stock solution for the three-day MTT cytotoxic assay was the same as the method described above for preparing the MTT stock solution for the one-day MTT cytotoxic assay. Briefly, CoLo 205, HT 29, and SW 620 cells were incubated in a 96-well culture plate (approximately 50,000 cancer cells in each well) for approximately 72 hours at approximately 37° C. in approximately 5% $CO_2$. MuJ-7 (approximately 20 μl per well) was added to the wells of all of the treated samples at time=0, 24, and 48 hours. CoLo 205, HT 29, and SW 620 cells not treated with MuJ-7 served as controls. Then, stock MTT solution (approximately 100 μg of MTT per well) was added to each well, and incubation continued for approximately 1 additional hour. The formazan crystals that formed inside the cells were dissolved with a detergent comprising approximately 10% sodium dodecyl sulfate and approximately 0.01 N HCl; and the optical density of each well was read spectrophotometrically at 540 nm. The percentage inhibition caused by MuJ-7 in CoLo 205, HT 29, and SW 620 was approximately 80%, approximately 18%, and approximately 41%, respectively.

EXAMPLE 4

Experiments were conducted to study the cytotoxic effect of MuJ-7 on 13 human tumor cell lines using the three-day MTT cytotoxic assay. These cells lines were: K562 (human leukemia), MOLT-4 (human lymphoma), L 132 (human lung carcinoma), MCF-7 (human breast), SW 620 (human colon), G 401 (human kidney), CoLo 205 (human colon), HuTu80 (human duodenum), Hu 746T (human stomach), HT29 (human colon), PC3 (human pancreas), SKO.007 (human myeloma), and SK.MEL.28 (human melanoma). The method for preparing the MTT stock solution for the three-day MTT cytotoxic assay was the same as the method described above for preparing the MTT stock solution for the one-day MTT cytotoxic assay. Briefly, cells from the 13 human tumor cell lines were incubated in a 96-well culture plate (approximately 50,000 cancer cells in each well) for approximately 72 hours at approximately 37° C. in approximately 5% $CO_2$. MuJ-7 (approximately 20 μl per well) was added to the wells of all of the treated samples at time=0, 24, and 48 hours. The controls were cells from the 13 tumor cell lines that were not treated with MuJ-7. Then, stock MTT solution (approximately 100 μg of MTT per well) was added to each well, and incubation continued for approximately 1 additional hour. The formazan crystals that formed inside the cells were dissolved with a detergent comprising approximately 10% sodium dodecyl sulfate and approximately 0.01 N HCl; and the optical density of each well was read spectrophotometrically at 540 nm. The approximate percentage of cytotoxicity (i.e., the percent inhibition) caused by MuJ-7 in each of thirteen cell lines is listed in Table 15A. No inhibition was observed in SKO.007 (human myeloma) and SK.MEL.28 (human melanoma).

TABLE 15A

The approximate percentage of cytotoxicity (i.e., the percent inhibition) caused by MuJ-7 in each of thirteen cell lines

| Cell Lines | Percentage of Cytotoxicity |
|---|---|
| K562 | 45 |
| MOLT-4 | 81 |
| L 132 | 36 |
| MCF-7 | 34 |
| SW 620 | 41 |
| G 401 | 35 |
| CoLo 205 | 80 |
| HuTu80 | 8 |
| HU 746T | 9 |
| HT29 | 18 |
| PC3 | 0 |
| SKO.007 | — |
| SK.MEL.28 | — |

EXAMPLE 5

Primary tumor cells of human colon adenocarcinoma were seeded in five separate flasks at a density of $10^4$ cells/ml. Five milliliters of RPMI 1640 containing 10% fetal calf serum were added to each flask. MuJ-7 (approximately 200 μl) was added to four of the flasks. MuJ-7 was not added to the fifth flask, which served as the control. Genomic DNA from the primary tumor cells of human colon adenocarcinoma was extracted after the cells were treated with MuJ-7 for different time intervals ranging from approximately 12 hours to approximately 96 hours. See the section below entitled "Description of Protocols" for a detailed description of the method used for the extraction of genomic DNA. The genomic DNA was extracted from the tumor cells in the first flask after approximately 12 hours; the genomic DNA was extracted from the tumor cells in the second flask after approximately 24 hours; the genomic DNA was extracted from the tumor cells in the third flask after approximately 48 hours; the genomic DNA was extracted from the tumor cells in the fourth flask after approximately 96 hours; and the genomic DNA was extracted from the tumor cells in the control flask after approximately 96 hours. The DNA of both untreated and treated cells was run on a 1% agarose gel using ethidium bromide for staining. The DNA of tumor cells treated with MuJ-7 for 48 and 96 hours formed a smear on the gel which is indicative of programmed cell death, while the DNA from untreated cells formed a sharp band at 10 kb, thus demonstrating that the DNA from untreated cells was intact. The DNA of tumor cells treated with MuJ-7 for 24 hours did not form a smear on the gel. Therefore, the time kinetic experiment in vitro showed that programmed cell death occurs between approximately 24 and 48 hours of treatment with MuJ-7.

Formulation of a dose of MuJ-7 for in vivo experiments:

A dose of the MuJ-7 formulation was prepared in the following way. A stock solution of each of the seven peptide analogs was first prepared using sterile phosphate buffered saline with an approximate pH of 7.4. The concentration of the peptide analog in each stock solution was approximately $10^{-3}$M. Aliquots of the seven peptides analogs were mixed together such that the MuJ-7 formulation contained approximately equal weights of each of the seven peptide analogs, with the combined weight of the seven peptide analogs in each dose of MuJ-7 being approximately 8 to 16 μg, depending upon the size of the dose. In MuJ-7, the concentration of $VIP_1$ was approximately $10^{-7}$M; the concentration of $VIP_2$ was approximately $10^{-8}$M; the concentration of $VIP_3$ was approximately $10^{-8}$M; the concentration of $SOM_1$ was approximately $10^{-9}$M; the concentration of $SOM_2$ was approximately $10^{-8}$M; the concentration of $BOM_1$ was approximately $10^{-8}$M; and the concentration of $SP_1$ was approximately $10^{-8}$M. The volume of this solution was made up with sterile RPMI 1640 to approximately 150 μl. RPMI 1640 is a cell culture medium that was developed at the Rosewell Park Memorial Institute. The components of RPMI 1640 are listed in Table 16.

TABLE 16

Components of RPMI 1640

| COMPONENTS | g/L |
|---|---|
| Calcium Nitrate.4 H2O | 0.1 |
| Magnesium sulfate(anhydrous) | 0.04884 |
| Potassium chloride | 0.4 |
| Sodium chloride | 6.0 |
| Sodium Phosphate Dibasic(anhydrous) | 0.8 |
| L-Arginine(free base) | 0.2 |
| L-Asparagine(anhydrous) | 0.05 |
| L-Aspartic acid | 0.02 |
| L-Cystine.2 HCl | 0.0652 |
| L-Glutamic acid | 0.02 |
| L-Glutamine | 0.03 |
| Glycine | 0.01 |
| L-Histidine(free base) | 0.015 |
| Hydroxy-L-Proline | 0.02 |
| L-Isoleucine | 0.05 |
| L-Leucine | 0.05 |
| L-Lysine.HCl | 0.04 |
| L-Methionine | 0.015 |
| L-Phenylalanine | 0.015 |
| L-Proline | 0.02 |
| L-Serine | 0.03 |
| L-Threnine | 0.02 |
| L-Tryptophan | 0.005 |
| L-Tyrosine.2 Na.2H$_2$O | 0.02883 |
| L-Valine | 0.02 |
| D-Biotin | 0.0002 |
| Choline chloride | 0.003 |
| Folic acid | 0.001 |
| myo-Inositol | 0.035 |
| Niacinamide | 0.001 |
| p-Amino Benzioc Acid | 0.01 |
| D-Pantothenic Acid(hemicalcium) | 0.00025 |
| Pyridoxine.HCl | 0.001 |
| Riboflavin | 0.0002 |
| Thiamin.HCl | 0.001 |
| Vitamin B-12 | 0.000005 |
| D-Glucose | 2.0 |
| Glutoathione(reduced) | 0.001 |
| HEPES | 5.958 |
| Phenol Red(sodium) | 0.0053 |

Throughout the following in viva experiments, control mice not injected with MuJ-7 were instead injected with RPMI 1640. The progressive growth of the tumors in the control mice indicates that RPMI 1640 is not critical to the effectiveness of MuJ-7.

In the following in vivo experiments, the tumor volume was calculated with the help of a vernier calliper. The shortest axis (a) and the longest axis (b) of the tumor was accurately measured, and the volume was calculated using the following formula:

$$\text{Tumor volume} = 0.4 \times a^2 \times b$$

The above-mentioned formula for tumor volume is derived from H. J. Winn, *National Cancer Institute Monograph* 2 (1959) 113–138.

In the following in vivo experiments, each tumor weight measurement was taken at the end of the experiment by sacrificing the mouse and resecting out the complete tumor growing superficially on the posterior side immediately below the skin over the muscular layer. The skin and any other tissues attached to the tumor were removed, and the tumor was immediately weighed on an analytical balance.

In vivo studies in tumor-bearing nude mice:

Out of 52 tumor-bearing nude mice treated with MuJ-7 according to the various in vivo protocols described in Examples 6–13, 49 mice showed complete or partial tumor regression. FIG. 1, which shows the effect on tumor regression of treatment onset time with MuJ-7, summarizes the mean tumor volume (in mm$^3$) for all of the mice in the in vivo protocols described in Examples 6–13 versus the day numbers. (Each data point in FIG. 1 represents the mean tumor volume of different numbers of mice from separate experiments.) In FIG. 1, the mice are grouped together into four categories: (1) untreated control mice ("Δ"); (2) treated mice ("+") that received their first dose of MuJ-7 by day 5; treated mice ("▲") that received their first dose of MuJ-7 after day 5 and by day 12; and treated mice ("∇") that received their first dose of MuJ-7 after day 12 and by day 20. The arrows indicate days 5, 12, and 20.

EXAMPLE 6

On day 1, ten BALB/c nude nu/nu mice were implanted with primary tumor cells of human colon adenocarcinoma (approximately 10 million tumor cells per mouse), and these mice received their first dose of MuJ-7 approximately on e hour after they were implanted with the tumor cells. The total daily dose of MuJ-7 for each treated mouse comprised approximately 1.143 μg of VIP$_1$, approximately 1.143 μg of VIP$_2$, approximately 1.143 μg of VIP$_3$, approximately 1.143 μg of SOM$_1$, approximately 1.143 μg of SOM$_2$, approximately 1.143 μg of BOM$_1$, and approximately 1.143 μg of SP$_1$. Thus, the total daily dose of MuJ-7 always contained approximately equal weights of each of the seven peptide analogs (VIP$_1$, VIP$_2$, VIP$_3$, SOM$_1$, SOM$_2$, BOM$_1$, and SP$_1$); and the total weight of these seven peptide analogs was approximately 8 μg. The total daily dose of MuJ-7 was divided into approximately three equal subdoses. Three times a day at approximately eight-hour intervals, a subdose was injected into each treated mouse. The first subdose of the day was injected into the tail vein; the second subdose of the day was injected into one gluteal muscle; and the third subdose of the day was injected into the other gluteal muscle. The treatment lasted for two weeks. Controls were randomly selected BALB/c nude nu/nu mice whose weights were similar to the weights of the ten treated mice. The control mice were subcutaneously injected with the same type and approximately the same number of human colon adenocarcinoma tumor cells as the treated mice. The control mice did not receive MuJ-7.

Figure 2:
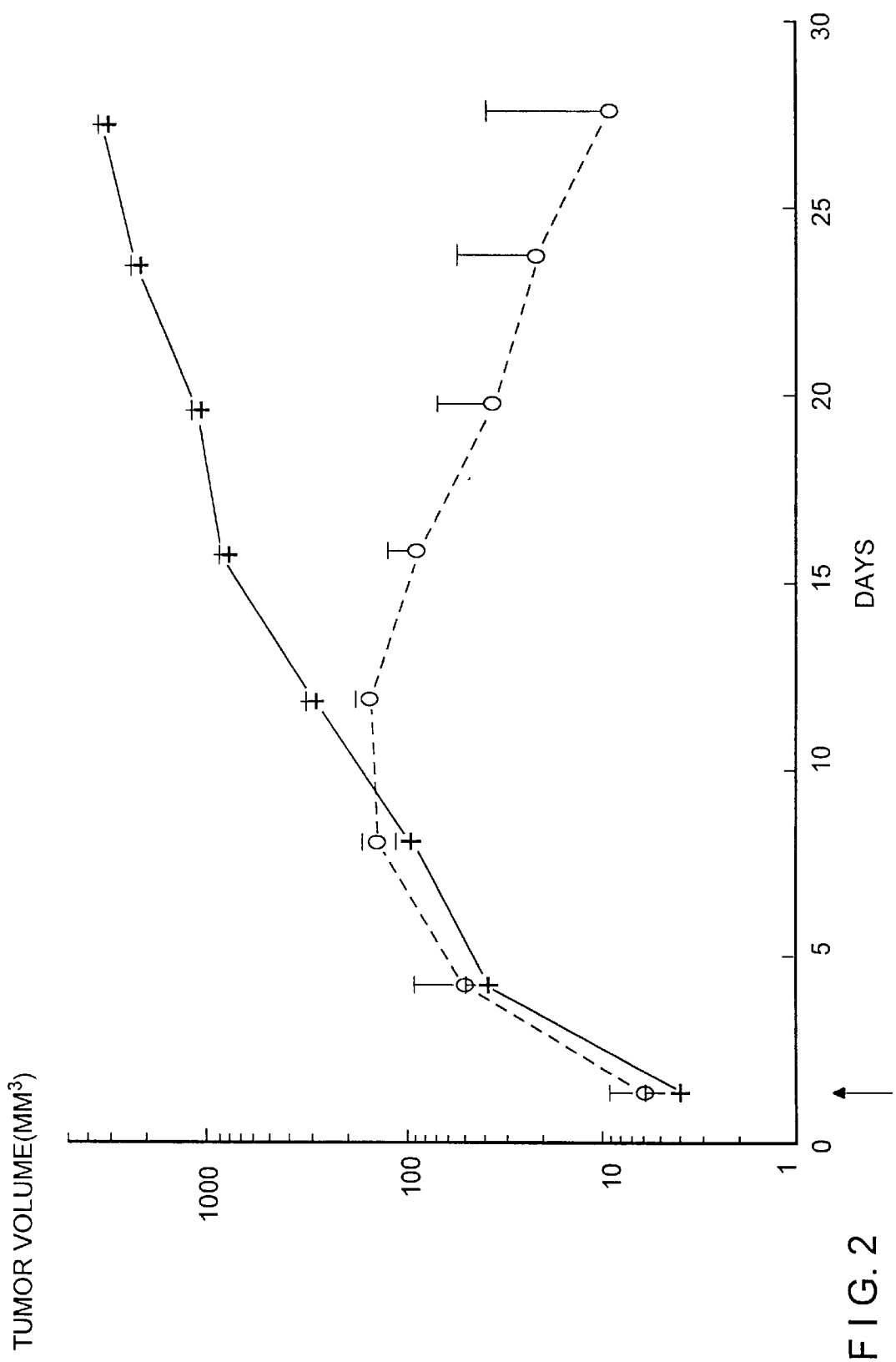
FIG. 2 is a graph of the mean tumor volume (in $mm^3$) of the treated mice ("○") and the untreated control mice ("+") versus the day numbers for the in vivo protocol described in Example 6.

The tumor volume in each treated and untreated mouse was recorded every four days. Table 17 lists the tumor volume in mm$^3$ for each treated mouse, and Table 18 lists the tumor volume in mm$^3$ for each control (untreated) mouse. FIG. 2 is a graph of the mean tumor volume (in mm$^3$) of the treated mice ("○") and the untreated control mice ("+") versus the day numbers. In FIG. 2, the arrow illustrates that the treated mice received their first dose of MuJ-7 approximately one hour after they were treated with tumor cells on day 1.

TABLE 17

Tumor volume in mm³ for each treated mouse; "R" stands for "complete regression" and indicates that tumor volume was not measurable

| | Tumor volume (mm³) on | | | | | | | |
|---|---|---|---|---|---|---|---|---|
| Mouse | Day 4 | Day 8 | Day 12 | Day 16 | Day 20 | Day 24 | Day 28 | Day 32 |
| 1 | 8 | 12 | 118 | 124 | 64 | R | | |
| 2 | 14 | 26 | 128 | 118 | 56 | 14 | R | |
| 3 | 6 | 42 | 156 | 124 | 32 | R | | |
| 4 | 8 | 156 | 124 | 148 | 96 | 24 | R | |
| 5 | 6 | 42 | 156 | 178 | 124 | 64 | 26 | R |
| 6 | 8 | 54 | 98 | 136 | 94 | 22 | R | |
| 7 | 3 | 26 | 114 | 92 | 36 | 4 | R | |
| 8 | 2 | 48 | 164 | 132 | 58 | 24 | 8 | |
| 9 | 4 | 28 | 96 | 134 | 78 | 58 | 46 | R |
| 10 | 6 | 46 | 116 | 132 | 76 | 64 | 60 | 58 |

TABLE 18

Tumor volume in mm³ for each control (untreated) mouse; the number in parentheses in the column labelled "Day 32" indicates the day of death of each mouse

| | Tumor Volume (mm³) on | | | | | | | |
|---|---|---|---|---|---|---|---|---|
| Mouse | Day 4 | Day 8 | Day 12 | Day 16 | Day 20 | Day 24 | Day 28 | Day 32 |
| 1 | 4 | 20 | 92 | 234 | 693 | 890 | 1578 | 2100(33) |
| 2 | 2 | 41 | 89 | 276 | 537 | 707 | 1678 | 1978(35) |
| 3 | 3 | 53 | 90 | 234 | 585 | 835 | 1357 | 2144(34) |
| 4 | 6 | 37 | 59 | 245 | 735 | 845 | 1467 | 2144(36) |
| 5 | 8 | 37 | 102 | 267 | 714 | 901 | 1786 | 2456(34) |

The treatment with MuJ-7 prevented tumor growth in approximately 90% of the treated mice. Furthermore, none of the treated mice died during the course of the experiment. By contrast, the control mice showed tumor growth, which eventually resulted in death of the mice.

EXAMPLE 7

Twenty BALB/c nude nu/nu mice, which were divided into two groups with ten mice in each group, were implanted on day 1 with primary tumor cells of human colon adenocarcinoma (approximately 10 million tumor cells per mouse). The group 1 mice received their first dose of MuJ-7 on day 12 (i.e., 11 days post implantation on the tumor cells on day 1). The group 2 mice received their first dose of MuJ-7 on day 20 (i.e., 19 days post implantation of the tumor cells on day 1). These twenty treated mice were injected for 14 days with a daily dose of MuJ-7. The total daily dose of MuJ-7 for each treated mouse comprised approximately 1.143 µg of $VIP_1$, approximately 1.143 µg of $VIP_2$, approximately 1.143 µg of $VIP_3$, approximately 1.143 µg of $SOM_1$, approximately 1.143 µg of $SOM_2$, approximately 1.143 µg of $BOM_1$, and approximately 1.143 µg of $SP_1$. Thus, the total daily dose of MuJ-7 always contained approximately equal weights of each of the seven peptide analogs ($VIP_1$, $VIP_2$, $VIP_3$, $SOM_1$, $SOM_2$, $BOM_1$, and $SP_1$); and the total weight of these seven peptide analogs was approximately 8 µg. The total daily dose of MuJ-7 was divided into approximately three equal subdoses. Three times a day at approximately eight-hour intervals, a subdose was injected into each treated mouse. The first subdose of the day was injected into the tail vein; the second subdose of the day was injected into one gluteal muscle; and the third subdose of the day was injected into the other gluteal muscle. Controls were five randomly selected BALB/c nude nu/nu mice whose weights were similar to the weights of the twenty treated mice in groups 1 and 2. (The same five mice served as controls for both the group 1 and the group 2 experiments.) The control mice were subcutaneously injected with the same type and approximately the same number of human colon adenocarcinoma tumor cells as the treated mice. The control mice did not receive MuJ-7.

In the group 1 mice, the tumor volumes were recorded every five days; and Table 19 lists the mean tumor volumes for the treated mice and the five control (untreated) mice. Three untreated control mice died on days 31, 32, and 34; and these deceased mice were excluded from measurements made after their day of death.

TABLE 19

Mean tumor volumes in mm³ for the treated group 1 mice and the five control (untreated) mice; "R" stands for "complete regression" and indicates that tumor volume was not measurable

| | Mean tumor volume (mm³) | |
|---|---|---|
| Day | Treated | Control |
| 17 | 5.1 | 54.9 |
| 22 | 9.8 | 122.1 |
| 27 | 5.6 | 253.3 |
| 32 | 5.88 | 1043.0 |
| 34 | Not measured | 1888.0 |

TABLE 19-continued

Mean tumor volumes in mm³ for the treated group 1 mice and the five control (untreated) mice; "R" stands for "complete regression" and indicates that tumor volume was not measurable

| Day | Mean tumor volume (mm³) | |
|---|---|---|
|  | Treated | Control |
| 37 | 11.7 | 1499.6 |
| 42 | 44.8 | 1978.1 |

Eight out of ten treated group 1 mice showed complete regression of the tumor by day 42. When complete regression occurred, measurements of tumor weight and tumor volume were not possible. Therefore, in Table 19 and in this paragraph, the mean tumor volume and the mean tumor weight for the treated group 1 mice on day 42 exclude the eight mice showing complete regression. As shown in Table 19, the mean tumor volume in group 1 mice treated with MuJ-7 increased from approximately 9.8 mm³ on day 22 to approximately 44.8 mm³ on day 42, while the mean tumor volume in the control (untreated) mice increased from approximately 122.1, mm³ on day 22 to approximately 1978.1 mm³ on day 42. The mean tumor weight on day 42 was approximately 51 mg in the two treated group 1 mice that did not show complete regression of the tumor, while the mean tumor weight on day 42 was approximately 1196 mg in untreated control mice.

Eight out of ten treated group 2 mice showed complete regression of the tumor by day 34 (i.e., 33 days post implantation with cancer cells). When complete regression occurred, measurements of tumor weight and tumor volume were not possible. Therefore, in this paragraph, the mean tumor volume and the mean tumor weight for the treated group 2 mice on day 34 exclude the eight mice showing complete regression. One control mouse died on day 31, one died on day 32, and one died on day 34. Therefore, in this paragraph, the mean tumor volume and the mean tumor weight for the control mice on day 34 exclude the two mice that died before day 34. In the group 2 mice, MuJ-7 caused a reduction in the mean tumor volume in the treated mice from approximately 105 mm³ on day 22 to approximately 3.1 mm³ on day 34, while the mean tumor volume in the untreated control mice increased from approximately 122.1 mm³ on day 22 to approximately 1888 mm³ on day 34. The mean tumor weight at the end of the experiment on day 34 was approximately 23 mg in the two treated group 2 mice that did not show complete regression of the tumor, while the mean tumor weight on day 34 was approximately 746 mg in the untreated control mice.

Figure 3:
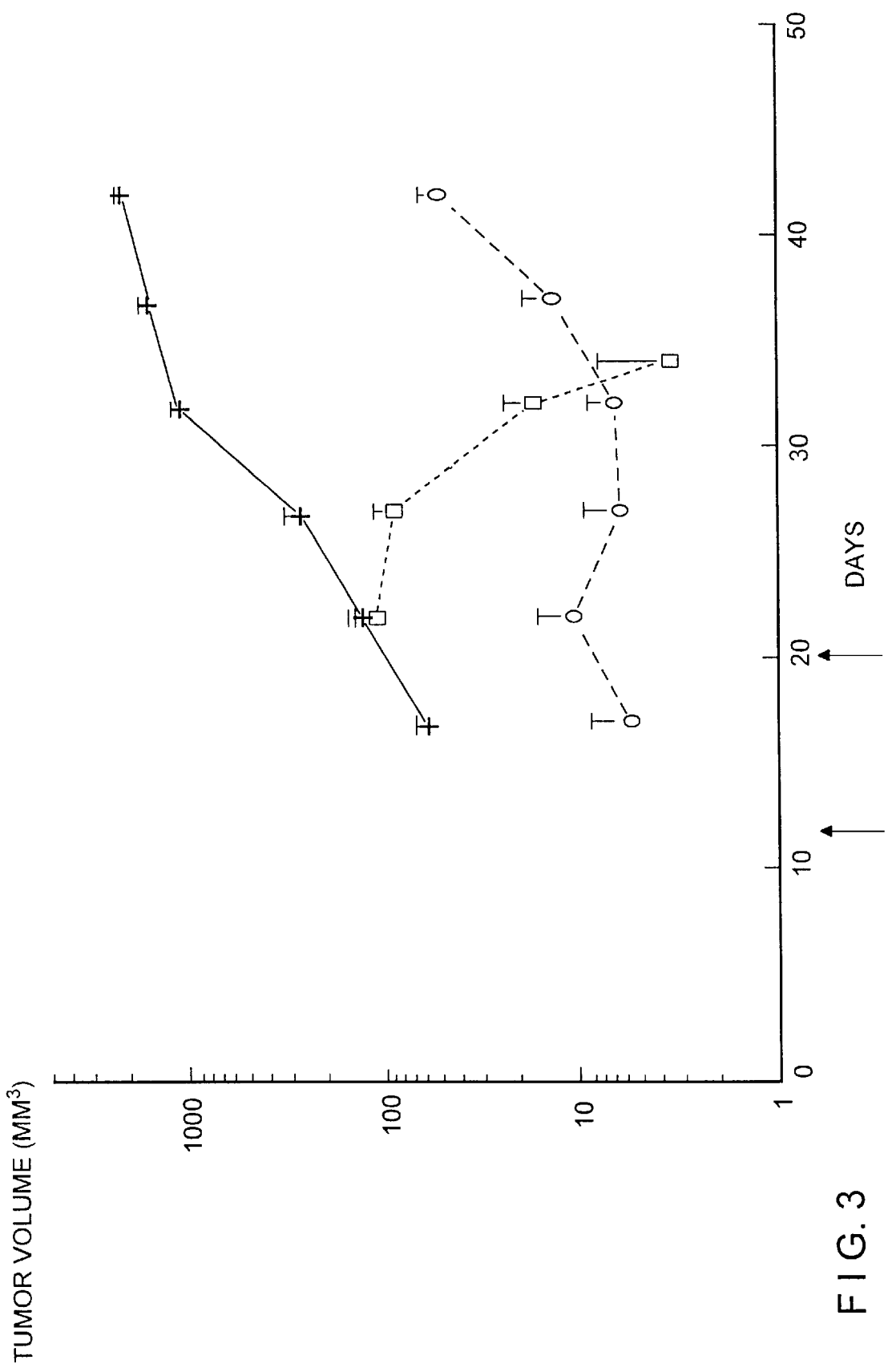
FIG. 3 is a graph of the mean tumor volume (in $mm^3$) of the group 1 treated mice ("○"), the group 2 treated mice ("□"), and the untreated control mice ("+") versus the day numbers for the in vivo protocol described in Example 7.

FIG. 3 is a graph of the mean tumor volume (in mm³) of the group 1 treated mice ("○"), the group 2 treated mice ("□"), and the untreated control mice ("+") versus the day numbers. In FIG. 3, the arrow under day number 12 indicates when the group 1 mice were first treated with MuJ-7; and the arrow under day number 20 indicates when the group 2 mice were first treated with MuJ-7.

EXAMPLE 8

The efficacy of MuJ-7 in the treatment of BALB/c nude nu/nu mice bearing primary colon tumors of human origin was tested using three human colon cancer cell lines (namely, HT 29, SW 620 and CoLo 205). In addition, the efficacy of MuJ-7 was also demonstrated in the treatment of BALB/c nude nu/nu mice injected with cells from human lung cancer line L 132. Briefly, for each of the above-mentioned human cancer cell lines (HT 29, SW 620, CoLo 205, and L 132), two nude mice, one of which served as a control, were subcutaneously injected on day 1 with approximately 12 million cancer cells; and treatment of the non-control mouse with MuJ-7 started 3–11 days after the injection. Once the treatment had started, each treated mouse was injected with MuJ-7 for 14 consecutive days, the daily dose of MuJ-7 being administered in approximately three equal subdoses. The daily dose of MuJ-7 for each treated mouse comprised approximately 1.143 μg of $VIP_1$, approximately 1.143 μg of $VIP_2$, approximately 1.143 μg of $VIP_3$, approximately 1.143 μg of $SOM_1$, approximately 1.143 μg of $SOM_2$, approximately 1.143 μg of $BOM_1$, and approximately 1.143 μg of $SP_1$. For the treated mouse with HT 29 cancer cells, treatment started on day 12 (i.e., 11 days post injection with the cancer cells); for the treated mouse with SW 620 cancer cells, treatment started on day 8 (i.e., seven days post injection with the cancer cells); for the treated mouse with CoLo 205 cancer cells, the treatment started on day 4 (i.e., three days post injection with the cancer cells); and for the treated mouse with L 132 cancer cells, the treatment started on day 5 (i.e., four days post injection with the cancer cells). The total daily dose of MuJ-7 was divided into approximately three equal subdoses. Three times a day at approximately eight-hour intervals, a subdose was injected into each treated mouse. The first subdose of the day was injected into the tail vein; the second subdose of the day was injected into one gluteal muscle; and the third subdose of the day was injected into the other gluteal muscle. Controls were randomly selected BALB/c nude nu/nu mice, whose weights were similar to the weights of the treated mice. The control mice were subcutaneously injected with the same type and approximately the same number of cancer cells as the treated mice. The control mice were not treated with MuJ-7.

Figure 4:
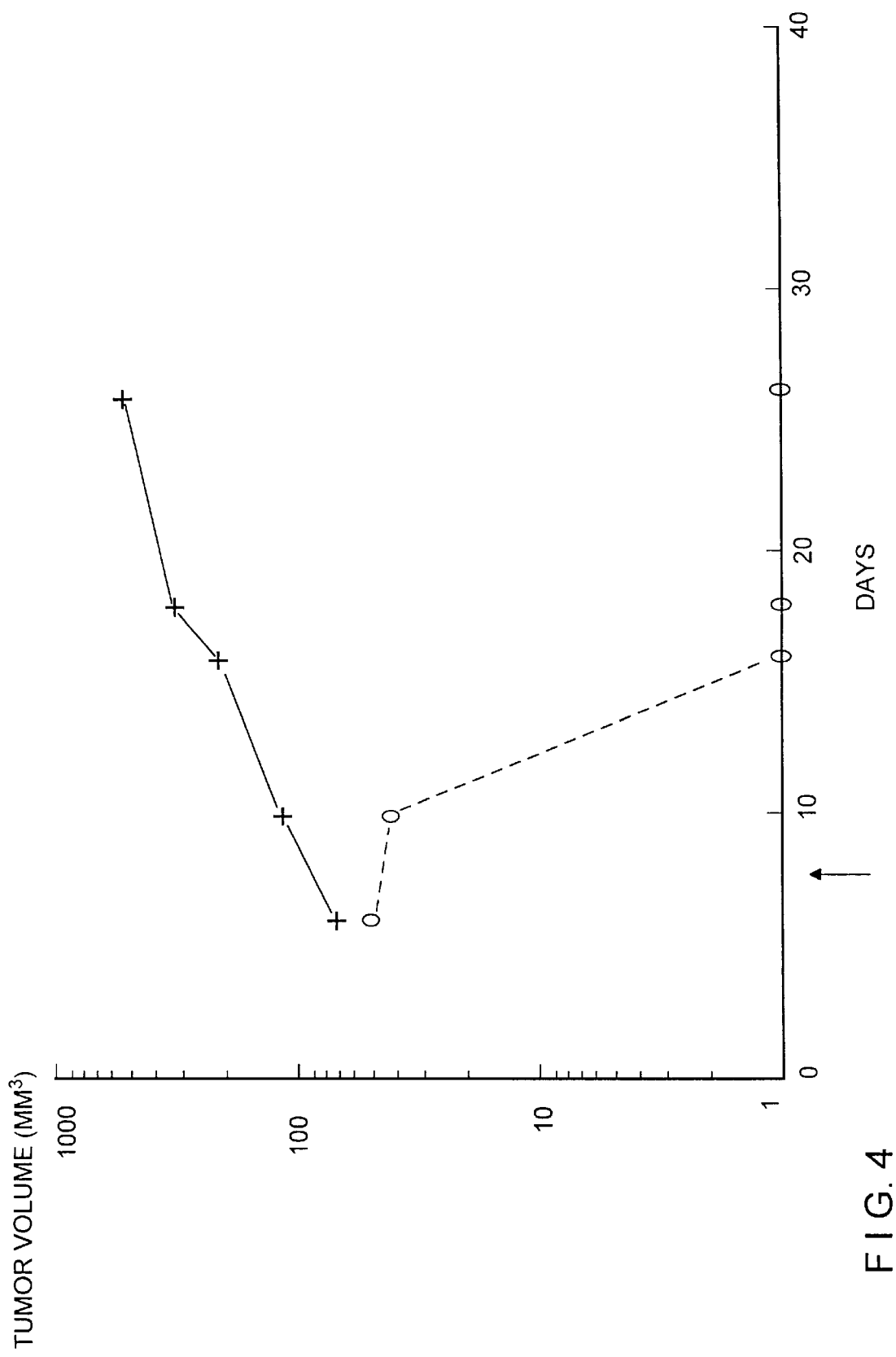
FIG. 4 is a graph of the tumor volume (in $mm^3$) of the treated mouse ("○") and the untreated control mouse ("+") versus the day numbers for the in vivo protocol with SW 620 cells described in Example 8.

For the experiments involving SW 620 cells, the tumor volume in the untreated control mouse increased from approximately 67.5 mm³ on day 6 to approximately 508.9 mm³ on day 26 (i.e., 25 days post injection with the cancer cells on day 1), at which time the mouse died because of the tumor, while the tumor volume in the mouse treated with MuJ-7 decreased from approximately 47.1 mm³ on day 6 to complete tumor regression on day 16 (after 9 days of treatment). Table 20 lists the tumor volume measurements in mm3 for the untreated control mouse and the treated mouse from day 6 until each mouse died. FIG. 4 is a graph of the tumor volume (in mm³) of the treated mouse ("○") and the untreated control mouse ("+") versus the day numbers, with the arrow indicating that the treated mouse received its first dose of MuJ-7 on day 8. Compared with the untreated mouse, the treated mouse, which died on day 87 (i.e., 86 days post injection with SW 620 cells on day 1), had an overall increase in survival time of approximately mately 244%. The percentage increase in survival time is calculated herein according to the following formula:

Percentage increase in survival time=$[(N_T-N_C)/N_C]\times 100$ where $N_T$ is the day number of the day of death (or the day number of the last known day of survival) minus the day number of the day of injection with cancer cells for the treated mouse and $N_C$ is the day number of the day of death minus the day number of the day of injection with cancer cells for the untreated control mouse

TABLE 20

Tumor volume in mm³ for the untreated control mouse and the treated mouse, both of which were injected with SW 620 cells on day 1; "R" stands for "regression" and indicates that the tumor volume was not measurable

| | Tumor volume (mm³) on | |
|---|---|---|
| Day No | Control | Treated |
| 6 | 67.5 | 47.1 |
| 10 | 112.9 | 39.8 |
| 16 | 202.4 | R |
| 18 | 314.8 | R |
| 26 | 508.9(Died) | R |
| 29 | — | R |
| 43 | — | R |
| 87 | — | R(Died) |

Figure 5:
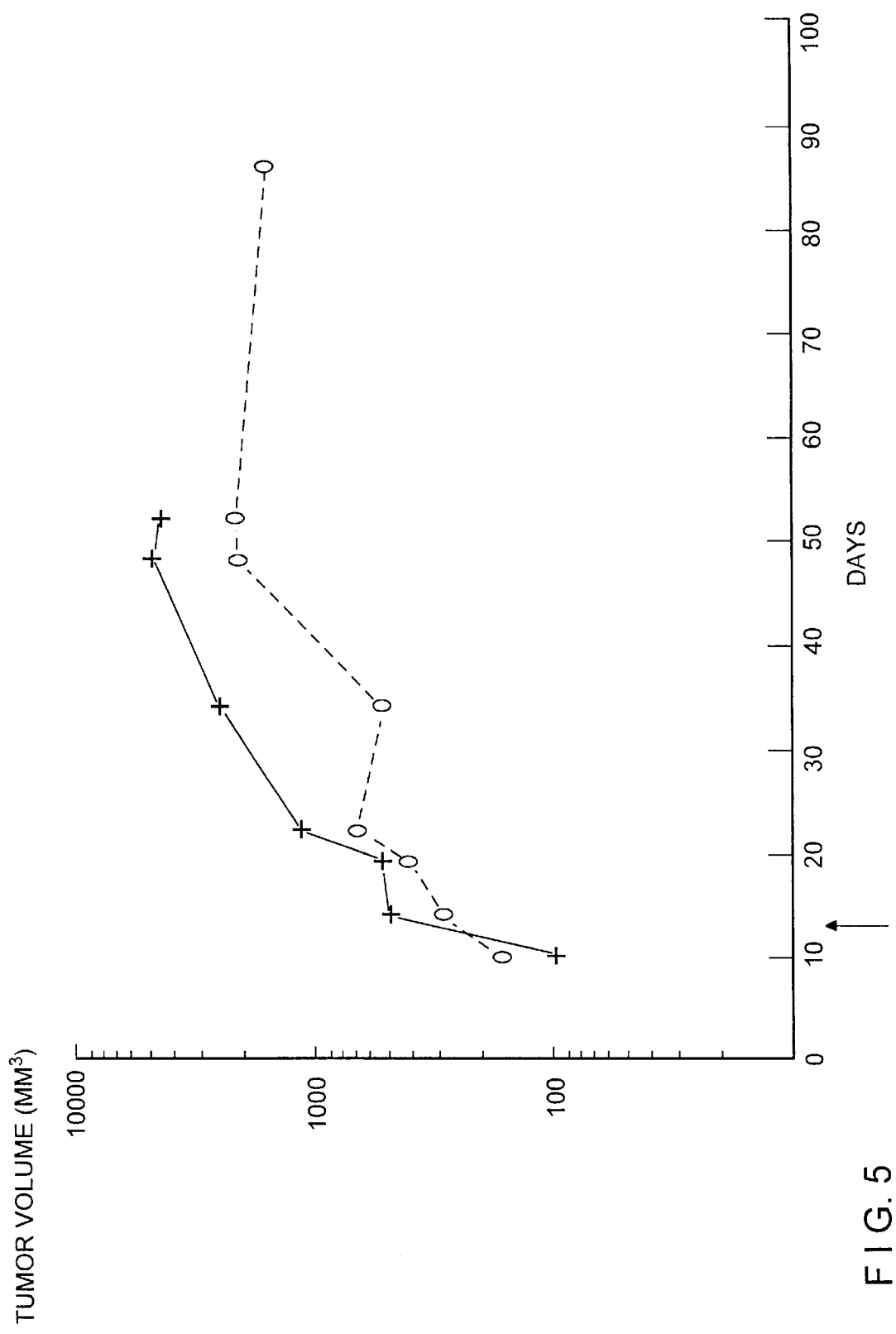
FIG. 5 is a graph of the tumor volume (in $mm^3$) of the treated mouse ("○") and the untreated control mouse ("+") versus the day numbers for the in vivo protocol with HT 29 cells described in Example 8.

For the experiments involving HT 29 cells, the tumor volume in the untreated mouse increased from approximately 95.1 mm³ on day 10 to approximately 4536.3 mm³ on day 52 (i.e., 51 days post injection with the cells on day 1), at which time the mouse died because of the tumor. By contrast, the tumor volume in the mouse treated with MuJ-7 increased relatively gradually from approximately 159.1 mm³ on day 10 to approximately 2192.7 mm³ on day 52, after which the tumor volume decreased to approximately 1556.4 mm³ on day 86 (i.e., 85 days post injection with the cancer cells). Table 21 lists the tumor volume measurements in mm³ for the untreated control mouse and the treated mouse from day 10 until each mouse died. FIG. 5 is a graph of the tumor volume (in mm³) of the treated mouse ("○") and the untreated control mouse ("+") versus the day numbers, with the arrow indicating that the treated mouse received its first dose of MuJ-7 on day 12. Compared with the untreated mouse, the treated mouse, which died on day 104 (i.e., 103 days post the injection with HT29 cells on day 1), had an overall increase in survival time of approximately 102%.

TABLE 21

Tumor volume in mm³ for the untreated control mouse and the treated mouse, both of which were injected with HT 29 cells on day 1

| | Tumor volume (mm³) on | |
|---|---|---|
| Day No | Control | Treated |
| 10 | 95.1 | 159.1 |
| 14 | 486.8 | 282.0 |
| 19 | 500.2 | 395.5 |
| 22 | 1161.8 | 655.1 |
| 34 | 2576.9 | 511.4 |
| 48 | 4974.8 | 2129.3 |
| 52 | 4536.3 (Died) | 2192.7 |
| 86 | — | 1556.4 |
| 104 | — | Died |

Figure 6:
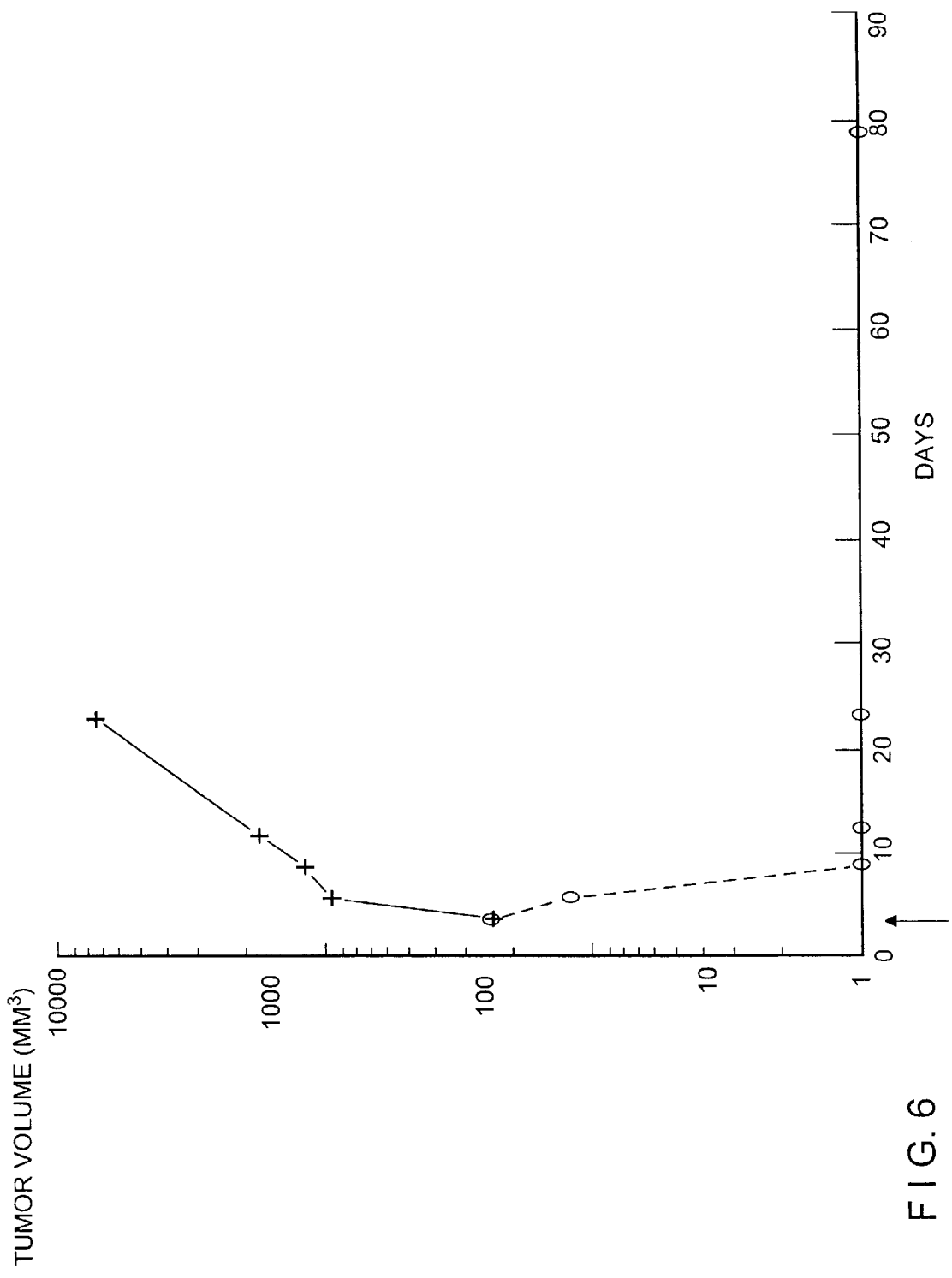
FIG. 6 is a graph of the tumor volume (in mm3) of the treated mouse ("○") and the untreated control mouse ("+") versus the day numbers for the in vivo protocol with CoLo 205 cells described in Example 8.

For the experiments involving CoLo 205 cells, the tumor volume in the untreated mouse increased from approximately 74.9 mm³ on day 3 to approximately 7344.9 mm³ on day 22 (i.e., 21 days post injection with the cancer cells on day 1), at which time the mouse died because of the tumor, while the tumor volume in the mouse treated with MuJ-7 decreased from approximately 78.2 mm³ on day 3 to complete tumor regression on day 8 (after 4 days of treatment). Table 22 lists the tumor volume measurements in mm³ for the untreated control mouse and the treated mouse from day 3 until each mouse died. FIG. 6 is a graph of the tumor volume (in mm³) of the treated mouse ("○") and the untreated control mouse ("+") versus the day numbers, with the arrow indicating that the treated mouse received its first dose of MuJ-7 on day 4. Compared with the untreated mouse, the treated mouse, which died on day 79 (i.e., 78 days post injection with CoLo 205 cells), had an overall increase in survival time of approximately 271%.

TABLE 22

Tumor volume in mm³ for the untreated control mouse and the treated mouse, both of which were injected with CoLo 205 cells on day 1; "R" stands for "regression" and indicates that the tumor volume was not measurable

| | Tumor volume (mm³) on | |
|---|---|---|
| Day No | Control | Treated |
| 3 | 74.9 | 78.2 |
| 5 | 497.6 | 29.8 |
| 8 | 668.9 | R |
| 11 | 1127.8 | R |
| 22 | 7344.9 (Died) | R |
| 79 | — | R Died |

Figure 7:
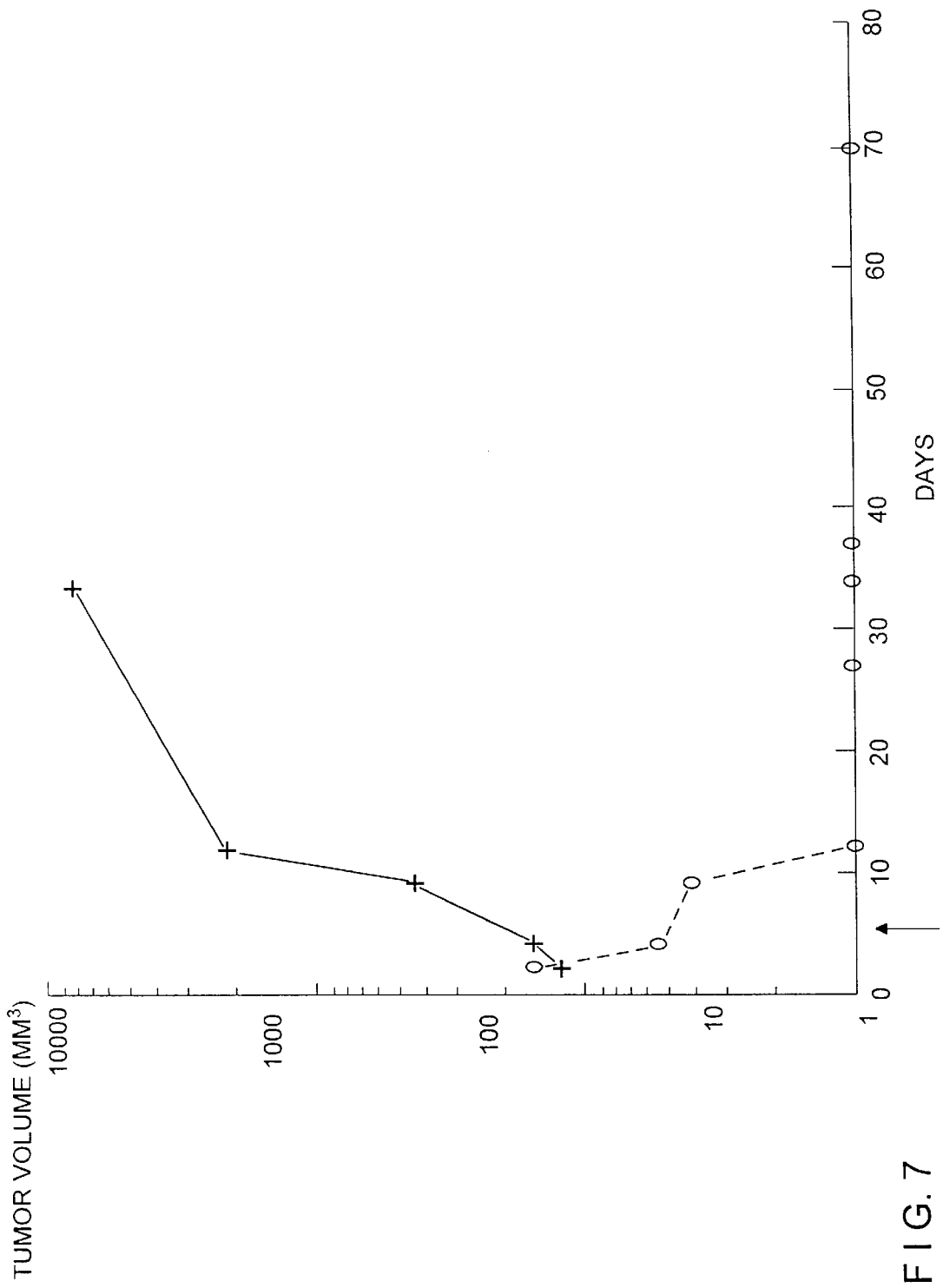
FIG. 7 is a graph of the tumor volume (in $mm^3$) of the treated mouse ("○") and the untreated control mouse ("+") versus the day numbers for the in vivo protocol with L 132 cells described in Example 8.

For the experiments involving L 132 cells, the tumor volume in the untreated mouse increased from approximately 28.5 mm³ on day 2 to approximately 7174.3 mm³ on day 34 (i.e., 33 days post injection with the the cancer cells on day 1), at which time the mouse died because of the tumor, while the tumor volume in the mouse treated with MuJ-7 decreased from approximately 38.3 mm³ on day 2 to complete regression on day 27 (after 22 days of treatment). Table 23 lists the tumor volume measurements in mm³ for the untreated control mouse and the treated mouse from day 2 until each mouse died. FIG. 7 is a graph of the tumor volume (in mm³) of the treated mouse ("○") and the untreated control mouse ("+") versus the day numbers, with the arrow indicating that the treated mouse received its first dose of MuJ-7 on day 5. Compared with the untreated mouse, the treated mouse, which died on day 70 (i.e., 69 days post injection with the L 132 cells), had an overall increase in survival time at approximately 109%.

TABLE 23

Tumor volume in mm³ for the untreated control mouse and the treated mouse, both of which were injected with L 132 cells on day 1; "R" stands for "regression" and indicates that the tumor volume was not measurable

| | Tumor Volume Measurements (mm³): L 132 | |
|---|---|---|
| Day No | Control | Treated |
| 2 | 28.5 | 38.3 |
| 4 | 38.5 | 9.1 |
| 9 | 147.2 | 5.9 |
| 12 | 1264.4 | 0.4 |
| 27 | — | R |
| 34 | 7174.3 (died) | R |
| 37 | — | R |
| 70 | — | R (died) |

EXAMPLE 9

Two BALB/c nude nu/nu mice were each implanted with approximately 10 million human colon adenocarcinoma cells on day 1. On day 22 (i.e., 21 days post implantation on day 1), one mouse began to receive intraperitoneally a daily dose of a combination of $VIP_1$, $VIP_2$, $VIP_3$, $SOM_1$, and SOM$_2$. Each day for fourteen days, this treated mouse received approximately 8 µg of the combination, the combination comprising approximately 1.6 µg of VIP$_1$, approximately 1.6 µg of VIP$_2$, approximately 1.6 µg of VIP$_3$, approximately 1.6 µg of SOM$_1$, and approximately 1.6 µg of SOM$_2$. The treated mouse received the last dose of the combination on day 35 (i.e., 34 days post implantation on day 1). At the end of the experiment on day 35, the tumor volume in the treated mouse was approximately 720 mm$^3$. The other mouse was untreated and served as a control. On day 35, the tumor volume in the untreated control mouse was approximately 3584 mm$^3$.

EXAMPLE 10

Three BALB/c nude nu/nu mice were each implanted with approximately 10 million human colon adenocarcinoma cells on day 1. On day 2 (i.e., one day post implantation on day 1), two mice each began to receive intraperitoneally a daily dose of a combination of VIP$_1$, VIP$_2$, VIP$_3$, SOM$_1$, and SOM$_2$. Once per day for fourteen days, each treated mouse received approximately 8 µg of the combination, the combination comprising approximately 1.6 µg of VIP$_1$, approximately 1.6 µg of VIP$_2$, approximately 1.6 µg of VIP$_3$, approximately 1.6 µg of SOM$_1$, and approximately 1.6 µg of SOM$_2$. (The daily dose was not divided into subdoses.) The treated mice received the last dose of the combination on day 15 (i.e., 14 days post implantation on day 1). At the end of the experiment on day 15, the tumor volume in one treated mouse was approximately 80 mm$^3$; and the tumor weight was approximately 0.149 g. On day 15, the tumor volume in the other treated mouse was approximately 0.8 mm$^3$; and the tumor weight was approximately 0.008 g. The third mouse was untreated and served as a control. On day 15, the tumor volume in the untreated control mouse was approximately 384 mm$^3$; and the tumor weight in the untreated control mouse was approximately 0.406 g.

EXAMPLE 11

Two BALB/c nude nu/nu mice were each implanted with approximately 10 million human colon adenocarcinoma cells on day 1. On day 2 (i.e., one day post implantation on day 1), one mouse began to receive a daily dose of a combination of VIP$_1$, VIP$_2$, VIP$_3$, SOM$_1$, and SOM$_2$. Each day for fourteen days, this treated mouse received approximately 8 µg of the combination, the combination comprising approximately 1.6 µg of VIP$_1$, approximately 1.6 µg of VIP$_2$, approximately 1.6 µg of VIP$_3$, approximately 1.6 µg of SOM$_1$, and approximately 1.6 µg of SOM$_2$. The daily dose of the combination was divided into approximately three equal subdoses. Three times a day at approximately eight-hour intervals, a subdose was given to each treated mouse. The first subdose each day was given intravenously, and the second and third subdoses each day were given via intramuscular injections. The treated mouse received the last dose of the combination on day 15 (i.e., 14 days post implantation on day 1). At the end of the experiment on day 15, the tumor volume in the treated mouse was approximately 0.8 mm$^3$; and the tumor weight was approximately 0.009 g. The other mouse was untreated and served as a control. On day 15, the tumor volume in the untreated control mouse was approximately 1728 mm$^3$; and the tumor weight in the untreated control mouse was approximately 2.18 g.

EXAMPLE 12

Three randomly selected BALB/c nude nu/nu mice were each implanted with approximately 16 million primary tumor cells of human colon adenocarcinoma on day 1. On day 21 (i.e., twenty days post implantation on day 1), on day 22, and on day 23, two of these mice were treated with a daily dose of MuJ-7. For each of these three days, the total daily dose of MuJ-7 for each treated mouse comprised approximately 1.143 µg of VIP$_1$, approximately 1.143 µg of VIP$_2$, approximately 1.143 µg of VIP$_3$, approximately 1.143 µg of SOM$_1$, approximately 1.143 µg of SOM$_2$, approximately 1.143 µg of BOM$_1$, and approximately 1.143 µg of SP$_1$; and the total weight of the seven peptide analogs was approximately 8 µg. On days 24 through 34, the total daily dose of MuJ-7 for each treated mouse comprised approximately 2.286 µg of VIP$_1$, approximately 2.286 µg of VIP$_2$, approximately 2.286 µg of VIP$_3$, approximately 2.286 µg of SOM$_1$, approximately 2.286 µg of SOM$_2$, approximately 2.286 µg of BOM$_1$, and approximately 2.286 µg of SP$_1$; and the total weight of the seven peptide analogs was approximately 16 µg. Each day, the total daily dose MuJ-7 was divided into approximately three equal subdoses. Three times a day at approximately eight-hour intervals, a subdose was given to each treated mouse. The first subdose each day was injected into the tail vein; the second subdose each day was injected into one gluteal muscle; and the third subdose each day was injected into the other gluteal muscle. The untreated third mouse, whose weight was similar to the weights of the two treated mice, served as a control and did not receive MuJ-7. Table 24 lists the tumor volume measurements in mm$^3$ through day 55 for the first treated mouse and until the second treated mouse and the control mouse died. Compared with the untreated control mouse, the first treated mouse, which survived at least until day 55 (i.e., 54 days post implantation with tumor cells on day 1), had an overall increase in survival of time of at least approximately 108%. Compared with the untreated control mouse, the second treated mouse, which died on day 38 (i.e., 37 days post implantation with tumor cells on day 1), has an overall increase in survival time of at least approximately 42%.

TABLE 24

Tumor volume in mm$^3$ for the two treated mice and the one untreated control mouse; each mouse was implanted with primary tumor cells of human colon adenocarcinoma on day 1

| | Tumor volume (mm$^3$) on | | |
|---|---|---|---|
| Day No | Treated (Mouse 1) | Treated (Mouse 2) | Control |
| 21 | 2396.2 | 4172.7 | 3297.4 |
| 24 | 2475.7 | 5940.2 | 7381.6 |
| 27 | Not measured | Not measured | 15783.5 (Died) |
| 28 | 1994.3 | 5910.3 | |
| 32 | 2210.0 | 6063.0 | |
| 36 | 2027.1 | 7877.4 | |
| 38 | Not measured | Died | |
| 41 | 1500.7 | | |
| 55 | 6256.7 | | |

EXAMPLE 13

On day 1, twenty-two BALB/c nude nu/nu mice were each implanted with approximately 10 million primary tumor cells of human colon adenocarcinoma. on day 15, twelve of these mice began to receive a daily dose of MuJ-7 for fourteen consecutive days. The daily dose of MuJ-7 for each treated mouse comprised approximately 1.143 µg of VIP$_1$, approximately 1.143 µg of VIP$_2$, approximately 1.143 µg of VIP$_3$, approximately 1.143 µg of SOM$_1$, approximately 1.143 µg of SOM$_2$, approximately 1.143 µg of BOM$_1$, and approximately 1.143 μg of SP$_1$. Thus, the total daily dose of MuJ-7 always contained approximately equal weights of each of the seven peptide analogs (VIP$_1$, VIP$_2$, VIP$_3$, SOM$_1$, SOM$_2$, BOM$_1$, and SP$_1$); and the total weight of these seven peptide analogs was approximately 8 μg. The total daily dose of MuJ-7 was divided into approximately three equal subdoses. Three times a day at approximately eight-hour intervals, a subdose was injected into each treated mouse. The first subdose of the day was injected into the tail vein; the second subdose of the day was injected into one gluteal muscle; and the third subdose of the day was injected into the other gluteal muscle. The ten untreated mice served as controls. The controls were ten randomly selected BALB/c nude nu/nu mice whose weights were similar to the weights of the twelve treated mice. The control mice were injected with the same type and approximately the same number of human colon adenocarcinoma tumor cells as the treated mice. The control mice did not receive MuJ-7.

Figure 8:
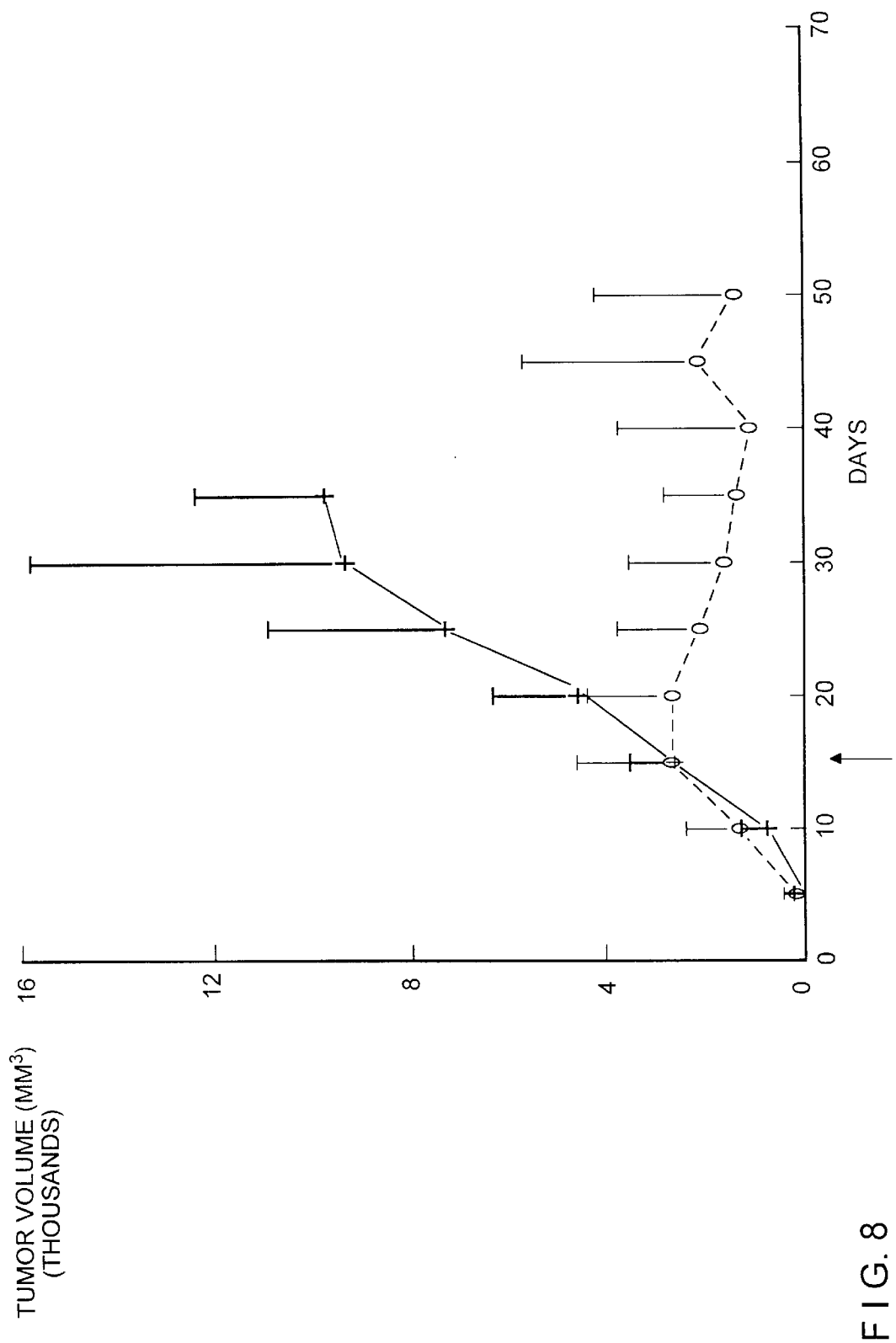
FIG. 8 is a graph of the mean tumor volume (in $mm^3$) of the treated mice ("○") and the untreated control mice ("+") versus the day numbers for the in vivo protocol described in Example 13.
Figure 9:
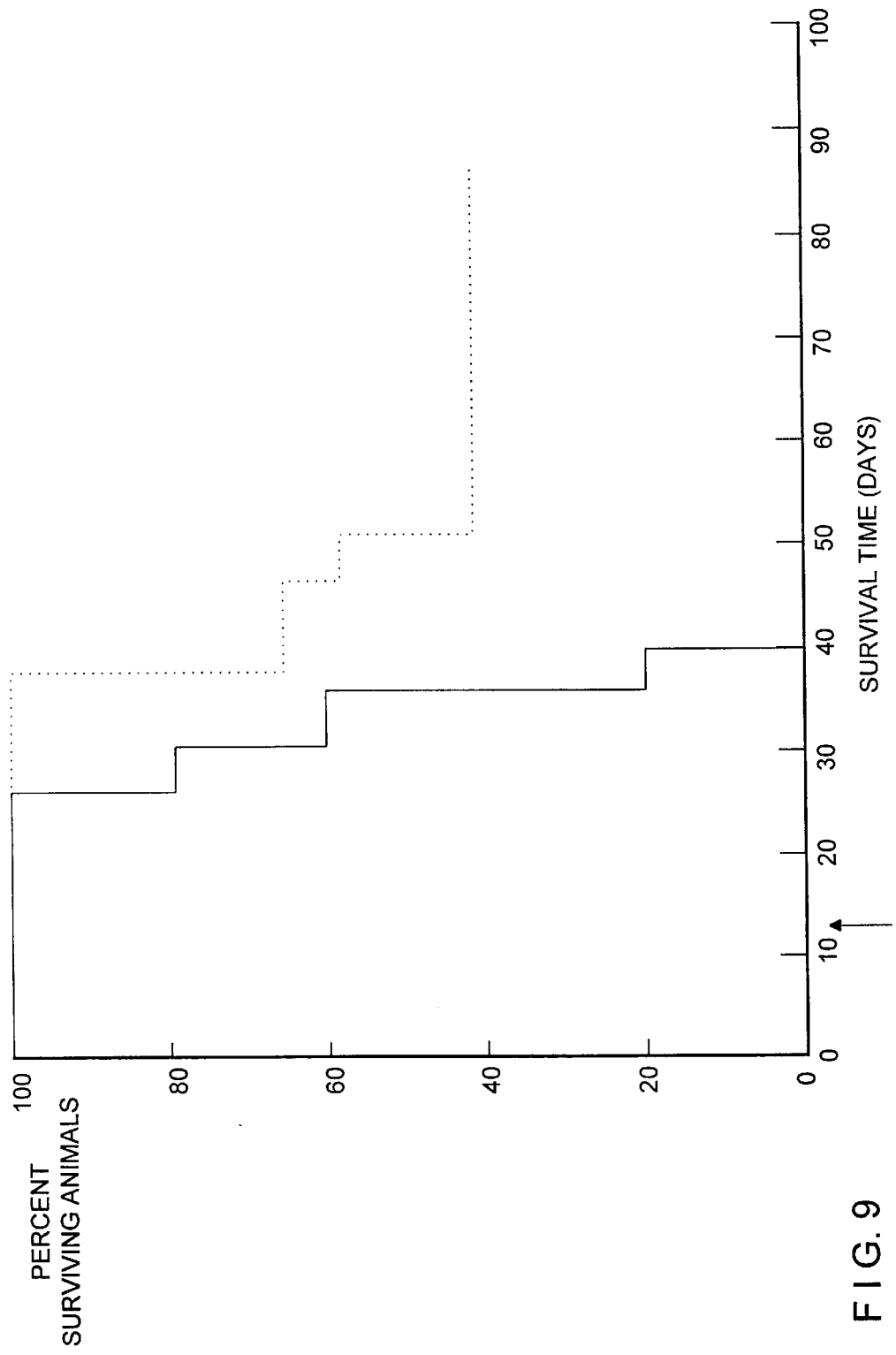
FIG. 9 is a graph of the percentage of surviving treated mice (dotted line) and the percentage of untreated control mice (solid line) versus the day numbers for the in vivo protocol described in Example 13.

The tumor volume in each treated and untreated mouse was recorded generally every five days. Table 25 lists the tumor volume in mm$^3$ for each of the twelve treated mice; and Table 26 lists the tumor volume in mm$^3$ for each of the ten untreated control mice.

of surviving treated mice (dotted line) and the percentage of untreated control mice (solid line) versus the day numbers. In FIGS. 8 and 9, the arrow illustrates that the treated mice received their first dose of MuJ-7 on day 15.

Eight of the ten control mice died from day 25 through day 35. By contrast, five of the twelve treated mice showed complete regression of the tumor; another five of the twelve treated mice showed partial regression of the tumor. Thus, ten of the twelve treated mice showed complete or partial regression of the tumor, while the two remaining treated mice (mouse number 11 and mouse number 13) had different outcomes. Treated mouse number 11 responded to therapy between day 15 and day 30, when it was treated with MuJ-7. After the treatment with MuJ-7 ended, the tumor in mouse 11 started to grow; and mouse 11 eventually died on day 50. Nevertheless, the survival time of treated mouse 11 still exceeded the average survival time of the untreated control mice. Treated mouse 3 also showed a decrease in the rate of tumor growth compared to the average rate of tumor growth in the untreated control mice. Although treated mouse 3 eventually died on day 50, the survival time of treated mouse 3 still exceeded the average survival time of the untreated control mice.

TABLE 25

Tumor volume in mm$^3$ for each treated mouse; "R" stands for "complete regression" and indicates that tumor volume was not measurable

| | Tumor volume (mm$^3$) of treated group on | | | | | | | | | | |
|---|---|---|---|---|---|---|---|---|---|---|---|
| Mouse | Day 5 | Day 10 | Day 15 | Day 20 | Day 25 | Day 30 | Day 35 | Day 40 | Day 45 | Day 50 | Day 55 |
| 1 | 38 | 949 | 2124 | 2547 | 1988 | 1654 | 1428 | dead | | | |
| 2 | 58 | 1011 | 2326 | 3423 | 2846 | 2210 | 1842 | dead | | | |
| 3 | 19 | 144 | 3076 | 4264 | 3862 | 2248 | 4264 | 6286 | 6848 | 7239 | dead |
| 4 | 10 | 251 | 626 | 1826 | 982 | 324 | 48 | R | | | |
| 5 | — | 404 | 2428 | 5564 | 3284 | 2128 | 1684 | dead | | | |
| 6 | 538 | 2317 | 809 | 624 | 102 | R | | | | | |
| 7 | 360 | 2804 | 1642 | 17 | 8 | 13 | R | | | | |
| 8 | 284 | 2247 | 6896 | 3248 | 2246 | 984 | 480 | 54 | 8 | R | |
| 9 | 31 | 2620 | 4470 | 3284 | 4286 | 2278 | 2020 | dead | | | |
| 10 | 348 | 1599 | 3437 | 2280 | 982 | 284 | 18 | R | | | |
| 11 | 54 | 183 | 218 | 155 | 191 | 265 | — | — | 7424 | dead | |
| 12 | — | 1715 | 3975 | 4307 | 4099 | 6646 | 2475 | — | — | 1976 | dead |

TABLE 26

Tumor volume in mm$^3$ for each untreated control mouse

| | Tumor Volume (mm$^3$) of control group on | | | | | | |
|---|---|---|---|---|---|---|---|
| Mouse | Day 5 | Day 10 | Day 15 | Day 20 | Day 25 | Day 30 | Day 35 |
| 1 | 437 | 1284 | 3297 | 7381 | 15783 | 21744 | dead |
| 2 | 216 | 896 | 2269 | 3409 | dead | | |
| 3 | 284 | 625 | 2290 | 3647 | 5915 | 6152 | dead |
| 4 | 12 | 916 | 3437 | 6142 | 9845 | dead | |
| 5 | 14 | 1715 | 3975 | 4307 | 4099 | 6646 | dead |
| 6 | 18 | 369 | 1299 | 2479 | 4270 | 5125 | dead |
| 7 | — | 316 | 2468 | 3247 | dead | | |
| 8 | 17 | 506 | 1241 | 3024 | 4364 | 5704 | 7805 |
| 9 | 45 | 1013 | 3156 | 6746 | 8702 | 10953 | 11657 |
| 10 | 54 | 183 | 2428 | 4807 | 5786 | dead | |

FIG. 8 is a graph of the mean tumor volume (in mm$^3$) of the treated mice ("○") and the untreated control mice ("+") versus the day numbers. FIG. 9 is a graph of the percentage Of the ten untreated control mice, two died on day 25, two died on day 30, four died on day 35, and two died after day 35. The five treated mice with complete tumor regression were monitored through day 55, and no tumor recurrence was observed. Of the remaining seven treated mice, four died on day 40, one died on day 50, two died on day 55; and, thus, the average survival time of these seven treated mice exceeded the average survival time of the ten untreated control mice.

Description of Protocols:

Indirect Immunofluorescence: About 100 μl of healthy adherent tumor cell suspension with a density of approximately 10$^4$ cells/ml from a 3-4 day old culture were plated on a round, sterile cover slip in a 24-day culture plate, and incubated at 37° C. in a CO$_2$ incubator. After 24 hours, when the tumor cells started to adhere to the culture surface, the wells were flooded with growth medium and incubated again at 37° C. in a CO$_2$ incubator. After approximately 4-5 days, the cover slips with adhering tumor cells were washed thoroughly in RPMI 1640 containing approximately 5% fetal calf serum (hereinafter referred to as "FCS") followed by washing in approximately 0.05 M phosphate buffered saline (hereinafter referred to as "PBS"), which contained approximately 5% FCS and which had an approximate pH of 7.4, followed by washing in plain PBS. The tumor cells on the cover slips were then incubated at approximately 37° C. for approximately one hour with a 1:50 dilution of the antipeptide polyclonal antibody. The cover slips were washed again as described above and the tumor cells incubated under the same conditions with a 1:200 dilution of anti-rabbit IgG-FITC conjugate. After washing, the cover slips were mounted in a medium made of carbonate-bicarbonate buffer and glycerol in a 1:1 ratio containing a crystal of para phenyl-diamine, and sealed in an inverted position on a glass slide with a clear varnish solution. The tumor cells were scanned under UV light on a Microphot FX microscope (Nikon).

Sandwich ELISA: Wells of a round-bottomed microtitre highly activated (Maxisorp) plate (Nunc, catalogue number 449824) were coated with 1 $\mu$g of the purified antibody in 100 $\mu$l of approximately mately 0.05 M phosphate buffered saline, which contained approximately 0.05% Tween 20 (PBS-T) and which had an approximate pH of 7.4, and were incubated for approximately one hour at approximately 37° C. After incubation, the wells were washed two times with PBS-0.2% Tween in an automatic plate washer (BDSL, UK). To each well 100 $\mu$l of Amicon concentrated culture supernatant of primary tumor cultures were added, followed by incubation for approximately one hour at approximately 37° C. The wells were washed three times as described previously. For color development, 25 $\mu$l of substrate (1 mg/ml orthophenyldiamine+1 $\mu$l $H_2O_2$) in citrate phosphate buffer (approximate pH of 5.5) was added to each well and incubated in the dark for approximately five minutes at approximately 37° C. The color development was terminated with the addition of 10 $\mu$l of 5N $H_2SO_4$. The absorbance in each well was determined at 490 nm on a multiscan microplate spectrophotometer (Biotech, USA).

Reverse Phase High Performance Liquid Chromatography: The supernatant of tumor cell cultures was run on a Waters C-18, 5 micron (46 mm×15 cm) column. The solvent system comprised two solvents that were run as a gradient. Solvent A consisted of approximately 0.1% trifluoroacetic acid, and solvent B consisted of approximately 80% acetonitrile in solvent A. A flow rate of 1.0 ml/minute was maintained and a gradient of approximately 40% to 100% solvent B in approximately 45 minutes was set up. A UV detector at a wavelength of 230 nm was used to detect the peptide.

Receptor-ligand assay: Tumor cells were grown to confluence in a 75 cm$^3$ flask, and the culture medium decanted. The cells were scraped off with the help of a rubber policeman and suspended in a minimum volume of binding buffer comprising approximately 5% bovine serum albumin (hereinafter referred to as "BSA") in RPMI 1640 to achieve a concentration of approximately 0.5×10$^6$ cells/50 $\mu$l. Increasing counts of I-125 peptides were added to the cells in the assay tube, and the volume was made up to approximately 200 $\mu$l with binding buffer. Radioactive counts were measured in each tube on a gamma counter. All the tubes were then incubated at approximately 37° C. for approximately one hour. In order to terminate the reaction, 2 ml of ice cold binding buffer were added to each tube and mixed thoroughly by vortexing. The tubes were centrifuged at approximately 2500 rpm (revolutions per minute) for approximately 10 minutes at approximately 4° C. The supernatant was discarded, and the tubes dried with blotting paper. Each tube was then counted on a gamma counter. The counts added to each tube were plotted against counts bound to plot the saturation curve.

The optimum cell number and tracer counts per tube were determined from the standard curve. This corresponded to the conditions at which there was no further increase in the number of bound counts on addition of tracer to a fixed cell concentration. Cold competition experiments were performed at these saturation conditions. A fixed cell concentration and tracer counts, as optimized earlier, were added to the assay tubes. This was followed by the addition of increasing concentrations of cold VIP, somatostatin, bombesin, and Substance P in duplicates to the tubes, and making up the volume to 200 $\mu$l with binding buffer. The tubes were then processed in a manner identical to the process described for preparation of the standard curve.

To calculate $K_D$(M) in moles and R(M/L) in moles per liter, the average counts of duplicate tubes were fed into LIGAND Software along with additional data such as molecular weight of labelled and unlabelled peptides, specific activity, dose units, the volume of the tubes, and the counting time. (LIGAND Software (version 3.0) is a radio-ligand binding analysis program, copyrighted by G. A. McPherson in 1986 and published and distributed by Elsevier, BIOSOFT, 68 Hills Road, Cambridge, United Kingdom.) The LIGAND Software performed a Scatchart Analysis by plotting on the Y axis the number of bound counts divided by the total number of counts added to each tube and plotting on the X axis the logarithm of the total number of counts added to each tube. The LIGAND Software used the intercept of the slope on the plot to calculate $K_D$(M) and R(M/L).

Extraction of Genomic DNA: The primary tumor cells were grown to confluence in vitro and the monolayer was washed twice with ice-cold Tris buffered saline (hereinafter referred to as "TBS"). Using a policeman, the cells were scraped into approximately 0.5 ml of TBS. The cell suspension was transferred to a centrifuge tube and stored on ice. The flask was washed with an additional 1 ml (approximately) of TBS, and washing was combined with cell suspension in the centrifuge tube. The cells were recovered by centrifugation at approximately 1500×g for approximately 10 min at approximately 4° C. The cells were resuspended in approximately 5–10 volumes of ice-cold TBS and centrifugation repeated. Finally, the cells were suspended in Tris edetate (hereinafter referred to as "TE," the TE having an approximate pH of 8.0) at a concentration of approximately 5×10$^7$ cells/ml. Ten milliliters of extraction buffer were added to 1 ml of cell suspension, and the solution was incubated for approximately 1 hour at approximately 37° C. Proteinase K to a final concentration of 100 $\mu$g/ml was added to this solution, and the solution was incubated in a gently shaking water bath for approximately 12 hours at approximately 50° C. The solution was then cooled to room temperature and transferred to a centrifuge tube. An equal volume of phenol-chloroform equilibrated with 0.5 M Tris.Cl (approximate pH of 8.0) was added, and the two phases were gently mixed for approximately 10 minutes. The phases were separated by centrifugation at approximately 5000×g for approximately 15 minutes at room temperature. The viscous aqueous phase was transferred to a centrifuge tube, and extraction was repeated twice with phenol-chloroform. Then, to the aqueous phase were added ½ volume of 7.5 M ammonium acetate and two volumes of ice-cold 100% ethanol. A string of DNA formed which was rinsed with 70% ethanol. This was decanted and dried on a Speedvac (Savant). The pellet was resuspended in TE.

The invention illustratively disclosed herein suitably may be practiced in the absence of any element which is not specifically disclosed herein.

The following claims are entitled to the broadest possible scope consistent with this application.

We claim:

1. A pharmaceutical composition comprising:

a therapeutically effective combination of peptide $SOM_2$ and at least four of peptides: $VIP_1$, $VIP_2$, $VIP_3$, $SOM_1$, $BOM_1$, and $SP_1$.

2. A pharmaceutical composition according to claim 1, the pharmaceutical composition further comprising a pharmaceutically acceptable carrier, diluent, or solvent.

3. A pharmaceutical composition as claimed in claim 1 comprising a therapeutically effective combination of $VIP_1$, $VIP_2$, $SOM_1$, $SOM_2$, and $BOM_1$.

4. A pharmaceutical composition as claimed in claim 1 comprising a therapeutically effective combination of $VIP_1$, $VIP_2$, $VIP_3$, $SOM_1$, $SOM_2$, $BOM_1$, and $SP_1$.

5. A pharmaceutical composition according to claim 4 wherein the concentration of $VIP_1$ is about $10^{-7}M$, the concentration of $VIP_2$ is about $10^{-8}M$, the concentration of $VIP_3$ is about $10^{-8}M$, the concentration of $SOM_1$ is about $10^{-9}$M, the concentration is $SOM_2$ about $10^{-8}$M, the concentration of $BOM_1$ is about $10^{-8}$M, and the concentration of $SP_1$ is about $10^{-8}$M.

6. A pharmaceutical composition as claimed in claim 4, wherein the molar ratio of $VIP_1:VIP_2:VIP_3:SOM_1:SOM_2:BOM_1:SP_1$ is about 1.0:0.1:0.1:0.01:0.1:0.1.

7. A pharmaceutical composition as claimed in claim 4, wherein the weight ratio of $VIP_1:VIP_2:VIP_3:SOM_1:SOM_2:BOM_1:SP_1$ is about 1:1:1:1:1:1:1.

8. A method of killing or inhibiting the multiplication of tumor cells or cancer cells in a human or other animal, the method comprising administering to the human or animal a therapeutically effective combination comprising peptide $SOM_2$ and at least four of peptides: $VIP_1$, $VIP_2$, $VIP_3$, $SOM_1$, $BOM_1$, and $SP_1$.

9. A method of killing or inhibiting the multiplication of tumor cells or cancer cells as claimed in claim 8, wherein the combination of peptides comprises a combination of $VIP_1$, $VIP_2$, $SOM_1$, $SOM_2$, and $BOM_1$.

10. A method of killing or inhibiting the multiplication of tumor cells or cancer cells as claimed in claim 8, wherein the combination of peptides comprises a combination of $VIP_1$, $VIP_2$, $VIP_3$, $SOM_1$, $SOM_2$, $BOM_1$, and $SP_1$.

11. A method of killing or inhibiting the multiplication of tumor cells or cancer cells as claimed in claim 10, wherein the concentration of $VIP_1$ is about $10^{-7}$M, the concentration of $VIP_2$ is about $10^{-8}$M, the concentration of $VIP_3$ is about $10^{-8}$M, the concentration of $SOM_1$ is about $10^{-9}$M, the concentration of $SOM_2$ is about $10^{-8}$M, the concentration of $BOM_1$ is about $10^{-8}$M, and the concentration of $SP_1$ is about $10^{-8}$M.

12. A method of killing or inhibiting the multiplication of tumor cells or cancer cells as claimed in claim 10, wherein the molar ratio of $VIP_1:VIP_2:VIP_3:SOM_1:SOM_2:BOM_1:SP_1$ is about 1.0:0.1:0.1:0.01:0.1:0.1.

13. A method of killing or inhibiting the multiplication of tumor cells or cancer cells as claimed in claim 10, wherein the weight ratio of $VIP_1:VIP_2:VIP_3:SOM_1:SOM_2:BOM_1:SP_1$ is about 1:1:1:1:1:1:1.

14. A method of killing or inhibiting the multiplication of tumor cells or cancer cells as claimed in claim 8, wherein said cells are in the colon or rectum of the human or animal to whom the combination of peptide is administered.

15. A method of preventing, inhibiting, or modulating in a human or other animal the hypersecretion of VIP, somatostatin, bombesin, Substance P, or a combination of VIP, somatostatin, bombesin, or Substance P, the method comprising administering to the human or animal a therapeutically effective combination comprising peptide $SOM_2$ and at least four of peptides: $VIP_1$, $VIP_2$, $VIP_3$, $SOM_1$, $BOM_1$, and $SP_1$.

16. A method as claimed in claim 15, wherein the therapeutically effective combination of peptides comprises a combination of $VIP_1$, $VIP_2$, $SOM_1$, $SOM_2$, and $BOM_1$.

17. A method as claimed in claim 15, wherein the therapeutically effective combination of peptides comprises a combination of $VIP_1$, $VIP_2$, $VIP_3$, $SOM_1$, $SOM_2$, $BOM_1$, and $SP_1$.

18. A method as claimed in claim 17, wherein the concentration of $VIP_1$ is about $10^{-7}$M, the concentration of $VIP_2$ is about $10^{-8}$M, the concentration of $VIP_3$ is about $10^{-8}$M, the concentration of $SOM_1$ is about $10^{-9}$M, the concentration of $SOM_2$ is about $10^{-8}$M, the concentration of $BOM_1$ is about $10^{-8}$M, and the concentration of $SP_1$ is about $10^{-8}$M.

19. A method as claimed in claim 17, wherein the molar ratio of $VIP_1:VIP_2:VIP_3:SOM_1:SOM_2:BOM_1:SP_1$ is about 1.0:0.1:0.1:0.01:0.1:0.1.

20. A method as claimed in claim 17, wherein the weight ratio of $VIP_1:VIP_2:VIP_3:SOM_1:SOM_2:BOM_i:SP_1$ is about 1:1:1:1:1:1:1.

* * * * *